United States Patent
Zhao et al.

(10) Patent No.: US 8,349,835 B2
(45) Date of Patent: Jan. 8, 2013

(54) AROMATIC RING FUSED TRIAZINE DERIVATIVES AND USES THEREOF

(75) Inventors: Linxiang Zhao, Shenyang (CN); Jinling Lv, Shenyang (CN); Rui Wang, Shenyang (CN); Dan Liu, Shenyang (CN); Yongkui Jing, Shenyang (CN)

(73) Assignee: Shenyang Pharmaceutical University, Shenyang (CN)

( * ) Notice: Subject to any disclaimer, the term of this patent is extended or adjusted under 35 U.S.C. 154(b) by 0 days.

(21) Appl. No.: 12/867,243

(22) PCT Filed: Feb. 10, 2009

(86) PCT No.: PCT/CN2009/000145
§ 371 (c)(1),
(2), (4) Date: Feb. 8, 2011

(87) PCT Pub. No.: WO2009/100655
PCT Pub. Date: Aug. 20, 2009

(65) Prior Publication Data
US 2011/0183972 A1 Jul. 28, 2011

(30) Foreign Application Priority Data
Feb. 14, 2008 (CN) .......................... 2008 1 0010387

(51) Int. Cl.
*A61K 31/53* (2006.01)
*C07D 253/04* (2006.01)
(52) U.S. Cl. ........................................ 514/243; 544/183
(58) Field of Classification Search .................. 514/243; 544/183
See application file for complete search history.

(56) References Cited

FOREIGN PATENT DOCUMENTS

| CN | 101 230 045 | 7/2008 |
|----|-------------|--------|
| CN | 101230045 | 7/2008 |
| EP | 09710751 | 8/2011 |
| WO | 2006/074223 | 7/2006 |
| WO | WO 2006/074223 | 7/2006 |

OTHER PUBLICATIONS

Lv, Jin- Ling. Design, Synthesis, and Antitumor Activities of Some Novel Substituted 1,2,3-Benzotriazines. Molecules. 13 (2008), 1427-1440.*
Stevens, H.N.E. et al. "Triazines and related products. III. Synthesis and rearrangement of 3,4-dihydro-4-imino-1,2,3-benzotriazines," Journal of the Chemical Society, Section C: Organic Chemistry, Chemical Society. Letchworth, GB, No. 6, Jan. 1, 1970, pp. 765-771, XP009150342, ISSN: 0022-4952.
Rewcastle, Gordon W. et al., "Tyrosine kinase inhibitors. 5. Synthesis and structure-activity relationships for 4-[(phenylmethyl)amino]- and 4-(phenylamino) quinazohnes as potent adenosine 5'-triphosphate binding site inhibitors of the tyrosine kinase domain of the epidermal growth factor receptor," Journal of Medicinal Chemistry, vol. 38, No. L8, 1995, pp. 3482-3487.
Baig, Ghouse Unissa et al., "Triazines and related products. Part 28. Conversion of 3-aryl-1-(2-cyanophenyl) riazenes into 3-arylquinazolin-4(3H)-ones with formamide," Journal of the Chemical Society, Perkin Transactions 1: Organic and Bio-Organic Chemistry (1972-1999), vol. 12, 1984, pp. 2765-2766.
Stevens, Malcolm F.G., "Triazines and related products. XIII. Decomposition of 4-arylamino-1,2,3-benzotriazines and their precursors in secondary amines," Journal of the Chemical Society, Perkin Transactions 1: Organic and Bio-Organic Chemistry (1972-1999), vol. 5, 1974, pp. 615-620.
Siddiqui, M. Shakil S. et al, "Triazines and Related Products, Part XI. Dimroth Rearrangement of 3-Substituted 3,4-Dihydro-4-imino-1,2,3-benzotriazines in Acetic Acid.," Journal of the Chemical Society, Perkin Transactions 1: Organic and Bio-Organic Chemistry (1972-1999), vol. 5, 1974, pp. 609-610.
Baig, Ghouse Unissa et al., "Triazines and Related Products. Part 28. Conversion of 3-aryl-1-(2-cyanophenyl) triazines into 3-arylquinazolin-4(3H)-ones with formamide, compounds 5a-5c," Journal of the Chemical Society, Perkin Transactions 1: Organic and Bio-Organic Chemistry 12:2765-2766, 1984.
Rewcastle, Gordon W., et al., "Tyrosine Kinase Inhibitors. 5. Synthesis and Structure—Activity Relationships for 4-[(Phenylmethyl)amino]- and 4-(Phenylamino)quinazolines as Potent Adenosine 5'-Triphosphate Binding Site Inhibitors of the Tyrosine Kinase Domain of the Epidermal Growth Factor Receptor," J. Med. Chem. 38(18):3482-3487, 1995.
Siddiqui, M. Shaquil S., et al., "Triazines and Related Products. Part XI. Dimroth Rearrangements of 3-Substituted 3,4-Dihydro-4-imino-1,2,3-benzotriazines in Acetic Acid, compounds 5a-5j," Journal of the Chemical Society, Perkin Transactions 1: Organic and Bio-Organic Chemistry 5: 609-610, 1974.
Stevens, Malcolm, F.G., "Triazines and Related Products. XIII Decomposition of 4-arylamino-1,2,3-benzotriazines and their precursors in secondary amines, compounds 1a-1i," Journal of the Chemical Society, Perkin Transactions 1: Organic and Bio-Organic Chemistry 5: 615-620, 1974.

* cited by examiner

*Primary Examiner* — Rebecca Anderson
*Assistant Examiner* — Samantha Shterengarts
(74) *Attorney, Agent, or Firm* — Barry L. Davison; Davis Wright Tremaine LLP

(57) ABSTRACT

The invention belongs to pharmaceutical field. The invention relates to the compounds according to Formula I, including their optically active forms, pharmaceutically acceptable salts or hydrates, and the pharmaceutical composition comprising thereof as active ingredient; uses in the preparation of vascular endothelial growth factor receptor tyrosine kinase inhibitors, and uses in the preparation of medicament for the treatment and/or prevention of cancer.

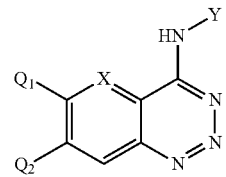

I

7 Claims, No Drawings

AROMATIC RING FUSED TRIAZINE DERIVATIVES AND USES THEREOF

CROSS REFERENCE TO RELATED APPLICATIONS

This application is the United States nationalization, under 35 U.S.C. §371, of International Application No. PCT/CN2009/000145, filed Feb. 10, 2009, which claims the benefit of priority to CN 200810010387.3, filed Feb. 14, 2008, both of which are incorporated by reference herein in their entirety.

FIELD OF THE INVENTION

The present invention belongs to the field of medical technology; specifically relates to Benzotriazines derivatives, their optically active compounds, and the pharmaceutically acceptable salts and hydrates. This invention also relates to the pharmaceutical composition comprising these compounds as active ingredient, uses in the preparation of vascular endothelial growth factor receptor tyrosine kinase inhibitors, and uses in the preparation of medicament for the treatment and/or prevention of cancer.

BACKGROUND OF THE INVENTION

Cancer, also known as malignant tumors, is a common disease that seriously threatens the human health. At present, mortality of cancer is still rising, but there lacks effective drugs on treating the common solid tumors. Most existing chemotherapy drugs kill cancer cells through interfering with some aspects in the cell division process, but they do not differentiate cancer cells from normal cells. Therefore, these drugs will also produce side effects while killing cancer cells.

Angiogenesis refers to the new vascular tissues which are generated by the endothelial cells on the basis of the existing vascular bed, thus to provide blood supply to the new tissues which are far away from the existing vascular system. In the physiological state of mature individuals, except during women's menstrual cycle, vascular endothelial cells are in a stable state, without vascular regeneration. The continuous state of angiogenesis is closely related to pathological conditions, such as tumor growth, metastasis, and wound healing.

The angiogenesis process is regulated by a variety of vascular growth regulators (TAFs). At present, more than 20 vascular growth regulators and correlation factors have been isolated and purified. Recently, some factors have been under extensive research, such as vascular endothelial factor (VEGF), transformation growth factor (TGF), fibroblast growth factor (FGF), platelet-derived growth factor (PDGF), angiogenin, grain-colony stimulating factor (GCSF), α-tumor necrosis factor (TNF-α), interleukin-8 (IL-8), proliferin, activators of integrins, hepatocyte growth factor (HGF), etc. The angiogenic inhibitors include thrombospondin, angiostatin, endostatin, etc.

Under the normal condition, there is a balance between angiogenic stimulators and inhibitors. When the angiogenic stimulators are at an up state, while the angiogenic inhibitors are at a down state, the angiogenesis mechanism is "open", and the tumor vessels regenerate. This is the angiogenesis switch balance hypothesis proposed by Hanahan et al.

The vascular endothelial cell growth factor (VEGF) can be secreted from a variety of tumor cells, and is the major inducer of angiogenesis, so it is at the core position of the tumor angiogenesis. VEGF binds to its receptor tyrosine kinase to achieve the signal transduction in vascular endothelial cells, thus inhibiting the activity of VEGF receptor tyrosine kinase can effectively inhibit the tumor angiogenesis.

VEGF receptor (VEGFR) tyrosine kinase is a promising anticancer target. The compounds that are already in the market or under clinical trials, such as Sutent, Vatalanib succinate (PTK787/ZK222584) and Zactima (ZD6474), all have the ability to inhibit the activity of VEGFR.

There is no report on the synthesis of benzo-triazine and pyridido-triazine and application of triazine derivatives in anti-cancer treatment in current literature.

SUMMARY OF THE INVENTION

This invention provides a series of benzotriazine and pyridotriazine derivatives as represented in Formula I below, and also relates to the use thereof in anticancer treatment.

Specifically, the present invention relates to a compound according to Formula I:

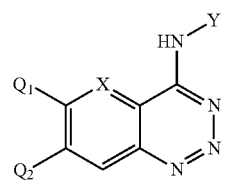

I

Wherein:
X is CH, $Q_1$ and $Q_2$ are same or different, and independently selected from: H and halogen, or $C_{1-5}$ alkoxy substituted with $R_1$, or
X is N, $Q_1$ and $Q_2$ are same or different, and independently selected from: H and halogen, or $C_{1-5}$ alkoxy substituted with $R_1$, wherein the $R_1$ is halogen, $C_3$-$C_7$-cycloalkyl, 5-10 number heterocycle, or 5-10 numbered heteroaryl, the cycloalkyl optionally has 1-2 carbon-carbon double bonds or triple bonds, and the heterocycle or heteroaryl has 1-4 hetero atoms selected from N, O, or S,
Y is $C_6$-$C_{10}$-aryl or 5-10 numbered heteroaryl; wherein the heteroaryl optionally has 1-4 hetero atoms selected from N, O, or S, and the Y is optionally substituted by one to three same or different $R_2$ independently selected from halogen, $NO_2$, CN, $CF_3$, —$OCF_3$, $C_{1-4}$-alkyl, $C_{1-4}$-alkoxymethyl, N,N-di-$C_{1-4}$alkylamino or $C_3$-$C_7$-cycloalkyl, and the cycloalkyl optionally has 1-2 carbon-carbon double bonds or triple bonds,
and optical isomers, pharmaceutically acceptable salts and hydrates thereof.

Preferably, the present invention relates to the following compounds of formula I and optical isomers, pharmaceutically acceptable salts and hydrates thereof, wherein $Q_1$ is H; $Q_2$ is H; X is CH; Y is phenyl, and the Y is optionally substituted by one to three same or different $R_2$ independently selected from halogen, $NO_2$, CN, $CF_3$, —$OCF_3$, $C_{1-4}$-alkyl, $C_{1-4}$-alkoxymethyl, N,N-di-$C_{1-4}$alkylamino or $C_3$-$C_7$-cycloalkyl, and the cycloalkyl optionally has 1-2 carbon-carbon double bonds or triple bonds.

The present invention also relates to the following preferred compounds: wherein $Q_1$ is —$OCH_3$, X is CH, Y is phenyl, and the Y is optionally substituted by one to three same or different $R_2$, $Q_2$ is $C_{1-5}$ alkoxy substituted with $R_1$; Wherein $R_2$ is halogen, $NO_2$, CN, $CF_3$, —$OCF_3$, $C_{1-4}$-alkyl, $C_{1-4}$-alkoxymethyl, N,N-di-$C_{1-4}$alkylamino or $C_3$-$C_7$-cycloalkyl, and the cycloalkyl optionally has 1-2 carbon-carbon double bonds or triple bonds; $R_1$ is halogen, $C_3$-$C_7$-cycloalkyl, 5-10 numbered heterocycle, or 5-10 numbered heteroaryl, the cycloalkyl optionally has 1-2 carbon-carbon double bonds or triple bonds, and the heterocycle or heteroaryl has 1-4 hetero atoms selected from N, O, or S.

More preferably, the present invention relates to the following compounds of formula I and optical isomers, pharmaceutically acceptable salts and hydrates thereof, wherein $Q_1$ is Cl, $Q_2$ is H, X is N, Y is phenyl, and the Y is optionally substituted by one to three same or different $R_2$, wherein $R_2$ is halogen, $NO_2$, CN, $CF_3$, —$OCF_3$, $C_{1-4}$-alkyl, $C_{1-4}$-alkoxymethyl, N,N-di-$C_{1-4}$alkylamino or $C_3$-$C_7$-cycloalkyl, and the cycloalkyl optionally has 1-2 carbon-carbon double bonds or triple bonds.

Furthermore, according to the general methods in the field of the present invention, the compounds of Formula I can react with acids to produce their pharmaceutically acceptable salts. The acids include inorganic acids and organic acids, preferably hydrochloric acid, hydrobromic acid, sulfuric acid, phosphoric acid, methylsulfonic acid, ethylsulfonic acid, toluene sulphonatic acid, benzene sulfonic acid, naphthalene disulfonic acid, acetic acid, propionic acid, lactic acid, trifluoroacetic acid, maleic acid, citric acid, fumaric acid, oxalic acid, tartaric acid, benzoic acid, p-toluene sulfonic acid, etc.

Some of the compounds of present invention may exist as stereoisomers including enantiomers and diastereomers. The present invention relates to enantiomers, diastereomers and their mixtures. The diastereomers may be separated from the racemic forms to the individual forms according to methods that are well known to those of ordinary skill in the art.

In addition, this invention also includes the prodrugs according to Formula I. According to the invention, the prodrug is a derivative of the general compounds of Formula I. They themselves may have weak or no activity, but after the administration, under physiological conditions (such as through metabolism, solvent decomposition or other means), they are transformed into the corresponding bioactive forms.

Unless otherwise indicated, the term "halogen" as employed herein includes fluorine, chlorine, bromine or iodine. The term "alkyl" as employed herein means straight chain or branched chain alkyl. The term "alkylene" as employed herein means straight chain or branched chain alkylene. The term "cycloalkyl" as employed herein means substituted or unsubstituted alkyl. The term "heteroaryl" as employed herein is monocyclic or multicyclic aromatic system including one or more heteroatoms selected from the group consisting of O, N, and S, for example, imidazolyl, pyridyl, pyrimidinyl, pyrazolyl, (1,2,3)- and (1,2,4)-triazolyl, pyrazinyl, tetrazolyl, furyl, thienyl, isoxazolyl, oxazolyl, pyrazolyl, pyrrolyl, thiazolyl, benzo-thienyl, benzo-furyl, benzimidazolyl, benzothiazolyl, indolyl, quinolyl, etc. The term "heterocycle" as employed herein to mean a monocyclic or multicyclic system including one or more heteroatoms selected from the group consisting of O, N, and S, for example, pyrrolidinyl, morpholinyl, piperazinyl, piperidyl, pyrazolidinyl, imidazolidinyl and thiazolinyl, etc.

The compounds of invention can have asymmetric center, and therefore exist in different enantiomeric and diastereomeric forms. The present invention relates to all the forms of the compounds according to the general Formula I, i.e., optical isomers, racemates and mixtures thereof. "Racemic" refers to a mixture containing the same amount of a pair of enantiomer.

The invention includes pharmaceutical compositions comprising the compounds according to the general Formula I, their optically active forms and their pharmaceutically acceptable salts or hydrates as the active ingredients, and pharmaceutically acceptable excipients. The "pharmaceutically acceptable excipients" refer to any drug diluents, adjuvant and/or carriers used in pharmaceutical field. Derivatives of the present invention can be used in combination with other active ingredients, as long as they do not have other adverse effects, such as allergic reactions.

Pharmaceutical compositions of this invention can be formulated into several dosage forms, containing a number of pharmaceutical excipients commonly used in the field, such as oral preparations (such as tablets, capsules, solution or suspension), injectable preparations (such as injectable solution or suspension, or lyophilized powder that can be injected immediately before use by adding water); topical preparations (such as ointment or solution).

The carriers of pharmaceutical compositions of this invention are commonly available types in the drug field, including: used in oral preparations as adhesives, lubricants, disintegrating agents, cosolvents, diluents, stabilizers, suspending agents, flavoring agents, etc.; used in injectable preparations as preservatives and stabilizers; used in local preparations as substrates, diluents, lubricants, preservatives, etc. Pharmaceutical preparations can be administered orally or intraperitoneally (e.g., intravenously, subcutaneously, intraperitoneally or locally). If certain drugs are unstable in the stomach condition, they can be made into coated tablets.

By in vitro screening and in vivo pharmacodynamic studies, we have found that the compounds of Formula I of the present invention have anti-tumor activity, and thus they can be used to prepare anti-cancers drugs in treating and/or preventing cancers such as breast, lung, colon, rectum, stomach, prostate, bladder, uterus, pancreas and ovarian cancers.

According to the invention, compounds of Formula I can be used as active ingredients to prepare drugs for treating and/or preventing cancers. The present invention also provides the methods of treating or preventing above diseases, including administrating effective amount of compounds to patients with or are prone to these diseases. The clinical dosage of the compounds depends on the subject, the specific administration routes and the severity of the diseases, and the best dosage should be determined by the specific doctors treating the patients.

The compounds of Formula I represented in invention can be used as the sole anti-cancer drugs, or in combination with one or more other anticancer drugs. The combined treatments are achieved by administering various anticancer drugs simultaneously, sequentially or separately.

The following embodiments and examples are used for further illustration of the compounds of the present invention and preparation methods thereof. It should be understood that the following implementation of the scope of cases and preparation of cases does not limit the scope of the present invention. Unless otherwise stated, compounds in the following cases with a chiral center exist as racemic mixtures. Unless otherwise stated, compounds in the following cases with two or more chiral centers exist as the racemic mixture of diastereomers. The invention includes all stereoisomers and both the racemic mixtures of such stereoisomers as well as the individual enantiomers/diastereomers that may be separated according to methods well known to those of ordinary skill in the art.

The compounds of the present invention may be prepared using methods known to those skilled in the art. Specifically, the compounds of the present invention with Formulae I can be prepared as illustrated by the exemplary reaction in Scheme 1.

Scheme 1

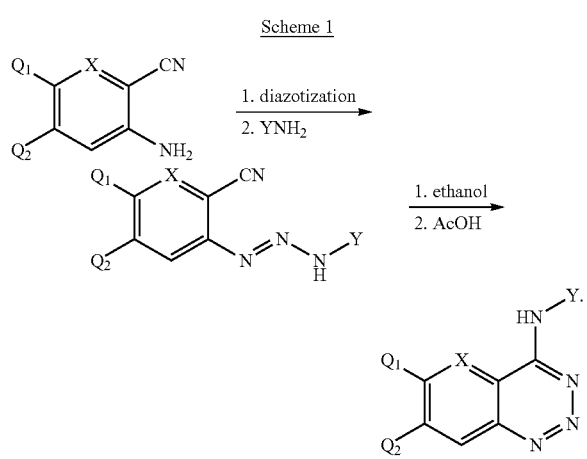

EMBODIMENTS

The purpose of these embodiments is to illustrate instead of limiting the scope of the invention. Reagents (analytical grade) were obtained from commercial suppliers and used without further purification unless otherwise noted. $^1$H-spectra were recorded by a Bruker ARX-300 instrument with tetramethylsilane as the internal standard. MS were determined on Agilent 1100 LC/MSD spectrometer

Example 1

The Synthesis of 4-(3-chloro-4-fluoroanilino)-benzo[d][1,2,3]triazine

Step A: General Procedure for the Synthesis of 1-(3-chloro-4-fluorophenyl)-3-(2-cyanphenyl)trinitrene

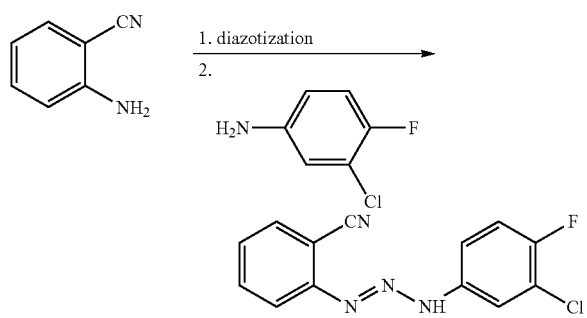

1.18 g (10 mmol) 2-Aminobenzonitrile was dissolved in 3.75 mL of concentrated $H_2SO_4$ while stirring and heating with an oil bath to achieve complete dissolution. 0.75 g (11 mmol) of sodium nitrite was added slowly to the ice-cooled solution of concentrated $H_2SO_4$ (3.75 mL). Once addition was complete, the mixture was heated to 80° C. under stirring for 30 min to obtain the sulphuric acid solution of 2-o-Aminobenzonitrile, which was cooled to 0° C. and then added dropwise to the ice-cooled solution of nitrosyl-sulfuric acid. The mixture was left to react under stirring at 0~5° C. for 45 min. Using sodium acetate to adjust the PH to 5~6, then added in dropwise 1.45 g (10 mmol) of 3-chloro-4-fluoro phenylamine (1.45 g, 10 mmol) dissolved in ethanol solution to react mixture at 0~5° C., stirred for 2 h, and kept using sodium acetate to maintain the pH value at 5-6. The solution was kept overnight, filtered and washed with water till colorless to yield the crude product. The crude product was purified on a silica gel column with petroleum ether:ethyl acetate (v/v)=15:1 to yield 0.6 g of the orange yellow crystal product with a recovery rate of 25.4%.

Step B: General Procedure for the Synthesis of 4-(3-chloro-4-fluoro)-benzo[d][1,2,3]triazine

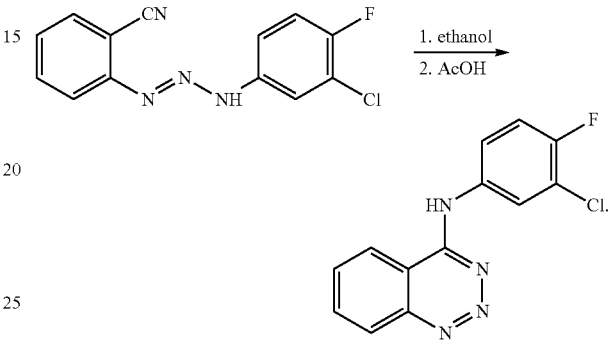

A mixture of 1-(3-chloro-4-fluorophenyl)-3-(2-cyanphenyl)-trinitrene (0.44 g, 2.0 mmol) and ethanol aqueous solution (70%, 30 ml) in anhydrous ethanol (10.0 mL) were added into a flask, then stirred and heated under reflux for 1 h. The solvent was evaporated to dryness under reduced pressure. Acetic acid glacial (20 mL) was added and the solution was heated to boiling and reacting for 1 h; then cooled, filtered and washed with water till colorless. The crude material was purified by recrystallization with anhydrous ethyl alcohol to yield a light brown solid product (0.11 g) with a recovery rate of 25.0%.

MS: (M+Na) 297.

$^1$H-NMR (DMSO, δ (ppm)): 7.53 (t, 1H), 7.87 (m, 1H), 8.06 (m, 1H), 8.14 (m, 1H), 8.26 (m, 2H), 8.58 (d, 1H), 10.07 (s, 1H).

Examples 2~10 were synthesised as described above by choosing appropriate materials.

Example 2

The Synthesis of 4-(4-fluoroanilino)-benzo[d][1,2,3]triazine

According to the synthesis method of Example 1, 4-Fluoro phenylamine instead of 3-chloro-4-fluoro phenylamine was used as the raw materials.

MS: (M+H) 241.

$^1$H-NMR (DMSO, δ (ppm)): 7.31 (t, 2H), 7.90 (m, 2H), 8.03 (m, 1H), 8.12 (m, 1H), 8.20 (d, 1H), 8.59 (d, 1H), 9.99 (s, 1H).

Example 3

The Synthesis of 4-(2-fluoroanilino)-benzo[d][1,2,3]triazine

According to the synthesis method of Example 1, 2-Fluoro phenylamine instead of 3-chloro-4-fluoro phenylamine was used as the raw materials.

MS: (M+H) 241.

$^1$H-NMR (DMSO, δ (ppm)): 7.33 (m, 1H), 7.36 (m, 1H), 7.41 (m, 1H), 7.61 (t, 1H), 8.03 (m, 1H), 8.13 (m, 1H), 8.21 (d, 1H), 8.53 (d, 1H), 10.09 (s, 1H).

Example 4

The Synthesis of 4-(3-chloroanilino)-benzo[d][1,2,3]triazine

According to the synthesis method of Example 1, 3-chloro phenylamine instead of 3-chloro-4-fluoro phenylamine was used as the raw materials.

MS: (M+H) 257.

$^1$H-NMR (DMSO, δ (ppm)): 7.26 (m, 1H), 7.49 (t, 1H), 7.89 (m, 1H), 8.06 (m, 1H), 8.14 (m, 2H), 8.24 (d, 1H), 8.63 (d, 1H), 10.04 (s, 1H).

Example 5

The Synthesis of 4-(3,5-difluoroanilino)-benzo[d][1,2,3]triazine

According to the synthesis method of Example 1, 3,5-difluoro phenylamine instead of 3-chloro-4-fluoro phenylamine was used as the raw materials.

MS: (M+H) 259.

$^1$H-NMR (DMSO, δ (ppm)): 7.05 (m, 1H), 7.83 (m, 2H), 8.09 (m, 1H), 8.17 (m, 1H), 8.27 (d, 1H), 8.62 (d, 1H), 10.14 (s, 1H).

Example 6

The Synthesis of 4-(4-trifluoromethoxyanilino)-benzo[d][1,2,3]triazine

According to the synthesis method of Example 1, 4-trifluoromethoxy phenylamine instead of 3-chloro-4-fluoro phenylamine was used as the raw materials.

MS: (M+H) 307.

$^1$H-NMR (DMSO, δ (ppm)): 7.48 (d, 2H), 8.05 (m, 3H), 8.14 (m, 1H), 8.24 (d, 1H), 8.62 (d, 1H), 10.09 (s, 1H).

Example 7

The Synthesis of 4-(3-trifluoromethoxyanilino)-benzo[d][1,2,3]triazine

According to the synthesis method of Example 1, 3-trifluoromethoxy-phenylamine instead of 3-Chloro-4-fluoro phenylamine was used as the raw materials.

MS: (M+H) 307.

$^1$H-NMR (DMSO, δ (ppm)): 7.19 (d, 1H), 7.59 (t, 1H), 8.02 (m, 1H), 8.07 (m, 1H), 8.13 (m, 1H), 8.18 (m, 1H), 8.26 (d, 1H), 8.64 (d, 1H), 10.11 (s, 1H).

Example 8

The Synthesis of 4-(3-fluoro-4-bromoanilino)-benzo[d][1,2,3]triazine

According to the synthesis method of Example 1, 3-fluoro-4-bromo-phenylamine instead of 3-Chloro-4-fluoro phenylamine was used as the raw materials.

MS: (M+H) 319.

$^1$H-NMR (DMSO, δ (ppm)): 7.78 (m, 2H), 8.07 (m, 1H), 8.18 (m, 2H), 8.18 (m, 1H), 8.26 (d, 1H), 8.63 (d, 1H), 10.13 (s, 1H).

Example 9

The Synthesis of 4-(3-trifluoromethyl-4-fluoroanilino)-benzo[d][1,2,3]triazine

According to the synthesis method of Example 1, 3-trifluoromethyl-4-fluoro-phenylamine instead of 3-chloro-4-fluoro phenylamine was used as the raw materials.

MS: (M+H) 309.

$^1$H-NMR (DMSO, δ (ppm)): 7.63 (t, 1H), 8.07 (m, 1H), 8.15 (m, 1H), 8.25 (d, 1H), 8.33 (m, 1H), 8.40 (m, 1H), 8.59 (d, 1H), 10.16 (s, 1H).

Example 10

The Synthesis of 4-(3,5-dichloroanilino)-1,2,3-benzotriazine

According to the synthesis method of Example 1, 3,5-dichloro-phenylamine instead of 3-chloro-4-fluoro phenylamine was used as the raw materials.

MS: (M+H) 291.

$^1$H-NMR (DMSO, δ (ppm)): 7.41 (s, 1H), 8.14 (m, 5H), 8.27 (d, 1H), 8.62 (d, 1H), 10.10 (s, 1H).

Example 11

The Synthesis of 6-methoxy-7-butoxy-4-anilino-benzo[d][1,2,3]triazine

Step A: General Procedure for the Synthesis of 3-methoxy-4-butoxybenzonitrile

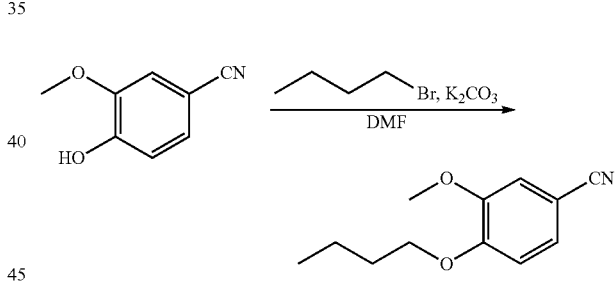

2-methoxy-4-cyano-phenol (0.25 g, 1.67 mmol) and anhydrous DMF (2.00 mL) were added into a flask, then cooled in a water bath while stirring. Several batches of $K_2CO_3$ (0.347 g, 2.50 mmol) were added to the mixture and stirred at 20° C. to react for 1 h. n-butyl bromine (0.23 ml, 2.14 mmol) was added into the mixture, which was stirred at room temperature overnight, then heated at 37° C. to react for 6 h. Poured the solution into a mixture of ice/$H_2O$ (25 mL), then stirred for 10 min, a precipitate was formed. Filtered, washed with $H_2O$, and air-dried to yield 0.361 g of white solid product with a recovery rate of 92%.

Step B: General Procedure for the Synthesis of 2-nitro-4-n-butoxy-5-methoxybenzonitrile

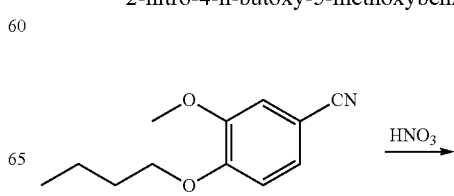

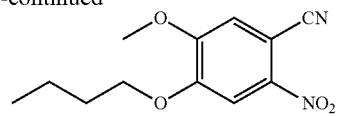

3-methoxy-4-n-butoxybenzonitrile (1.282 g, 6 mmol) and nitric acid (6 mL) were added into a round bottom flask, heated to 30° C. to react for 2 h, poured into ice-water; after complete stirring, the solution was filtered, washed with water and air-dried to yield 1.495 g of light yellow solid product with a recovery rate of 96%.

Step C: General Procedure for the Synthesis of 2-cyano-4-methoxy-5-n-butoxy phenylamine

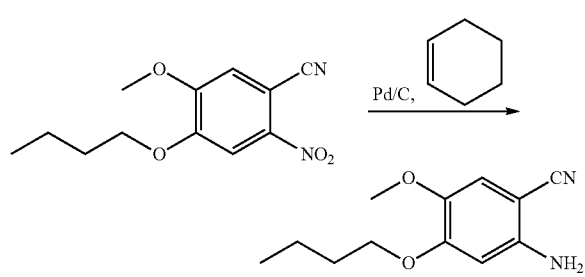

2-nitro-4-butoxy-5-methoxybenzonitrile (0.563 g, 2.24 mmol), Pd/C (0.035 g) and anhydrous ethanol (25.0 mL) were added into a round bottom flask. The solution was stirred and heated under reflux. Cyclohexene (1.15 mL) was added and refluxed until the disappearance of the starting materials as monitored by TLC. After cooling, the resulting mixture was filtered and washed with ethanol. The filtrate was concentrated to yield a solid product. The crude product was suspended in anhydrous ethanol (4 ml), stirred and heated to 40° C. to react for 30 min, then cooled to room temperature, filtered and air-dried to yield 0.352 g of light yellow solid product with a recovery rate of 71%.

Step D: General Procedure for the Synthesis of 1-phenyl-3-(2-cyan-4-methoxy-5-n-butoxyphenyl) triazene

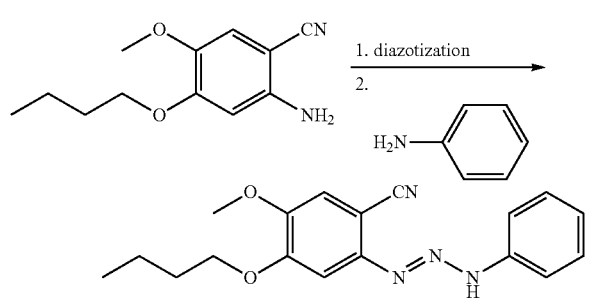

0.22 g (1 mmol) 2-cyano-4-methoxy-5-n-butoxyphenylamine and 3 mL (10 mol/L) hydrochloric acid were added into a round bottom flask. The solution was cooled to 0° C. and diazotized with sodium nitrite (0.072 g, 1 mmol) dissolved in water (1.0 mL), which was added dropwise to the solution. The mixture was stirred to react for 20 min. After adjusting the pH to 5~6 with sodium acetate, the ethanol solution of aniline (0.093 g, 1 mmol) was added dropwise to the reaction mixture to react for 2 h under stirring, while maintaining the reaction temperature at between 0~5° C., and using sodium acetate to keep the pH value at 5-6. The solution was kept overnight, filtered, and washed with water till colorless. The crude product was purified on a silica gel column with petroleum ether:ethyl acetate (v/v)=15:1 to yield 0.154 g of orange-yellow solid crystal product with a recovery rate of 47.5%.

Step E: General Procedure for the Synthesis of 6-methoxy-7-n-butoxy-4-anilino-benzo[d][1,2,3] triazine

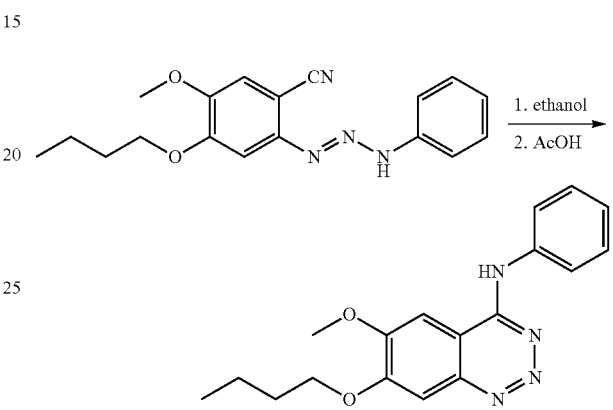

1-phenyl-3-(2-cyan-4-methoxy-5-n-butoxyphenyl)triazene (0.154 g, 0.47 mmol) and 70% ethanol (30.0 mL) were added into a flask. The solution was heated and refluxed to react for 1 h, then was evaporated under reduced pressure to dryness. Acetic acid glacial (20.0 mL) was added and the solution was refluxed for 1 h, cooled, filtered and washed with water till colorless. The crude product was purified by recrystallization with anhydrous ethanol to yield 0.121 g of light brown solid product with a recovery rate of 78.6%.

MS: (M+H) 325.

$H^1$-NMR (DMSO, δ (ppm)): 0.97 (t, 3H), 1.51 (m, 2H), 1.81 (m, 2H), 4.03 (s, 3H), 4.24 (t, 2H), 7.18 (t, 1H), 7.45 (t, 2H), 7.56 (s, 1H), 7.83 (d, 2H), 7.92 (s, 1H), 9.59 (s, 1H).

Compounds 12-77 were synthesised as described above by choosing appropriate materials Example 12

The Synthesis of 6-methoxy-7-n-butoxy-4-(3-fluoro-4-bromoanilino)-benzo[d][1,2,3]triazine According to the synthesis method of Example 11, 3-fluoro-4-bromo-phenylamine instead of phenylamine was used as the raw materials.

MS: (M+H) 421.

$H^1$-NMR (DMSO, δ (ppm)): 0.97 (t, 3H), 1.49 (m, 2H), 1.81 (m, 2H), 4.04 (s, 3H), 4.25 (t, 2H), 7.61 (s, 1H), 7.67 (m, 1H), 7.76 (m, 1H), 7.89 (s, 1H), 8.14 (d, 1H), 9.75 (s, 1H).

Example 13

The Synthesis of 6-methoxy-7-n-butoxy-4-(3,5-dichloroanilino)-benzo[d][1,2,3]triazine According to the synthesis method of Example 11, 3,5-dichloro-phenylamine instead of phenylamine was used as the raw materials.

MS: (M+H) 393.
H$^1$-NMR (DMSO, δ (ppm)): 0.97 (t, 3H), 1.49 (m, 2H), 1.81 (m, 2H), 4.05 (s, 3H), 4.25 (t, 2H), 7.36 (s, 1H), 7.62 (s, 1H), 7.88 (s, 1H), 8.10 (s, 1H), 9.72 (s, 1H).

Example 14

The Synthesis of 6-methoxy-7-n-butoxy-4-(3,5-difluoroanilino)-benzo[d][1,2,3]triazine According to the synthesis method of Example 11, 3,5-difluoro-phenylamine instead of phenylamine was used as the raw materials.
MS: (M+H) 361.
H$^1$-NMR (DMSO, δ (ppm)): 0.97 (t, 3H), 1.49 (m, 2H), 1.81 (m, 2H), 4.05 (s, 3H), 4.25 (t, 2H), 7.00 (t, 1H), 7.62 (s, 1H), 7.76 (d, 2H), 7.91 (s, 1H), 9.81 (s, 1H).

Example 15

The Synthesis of 6-methoxy-7-n-butoxy-4-(3,4-dichloroanilino)-benzo[d][1,2,3]triazine According to the synthesis method of Example 11, 3,4-dichloro-phenylamine instead of phenylamine was used as the raw materials.
MS: (M+H) 393.
H$^1$-NMR (DMSO, δ (ppm)): 0.97 (t, 3H), 1.50 (m, 2H), 1.81 (m, 2H), 4.04 (s, 3H), 4.25 (t, 2H), 7.61 (s, 1H), 7.70 (d, 1H), 7.91 (m, 2H), 8.31 (m, 1H), 9.71 (s, 1H).

Example 16

The Synthesis of 6-methoxy-7-n-butoxy-4-(4-chloroanilino)-benzo[d][1,2,3]triazine According to the synthesis method of Example 11, 4-chloro phenylamine instead of phenylamine was used as the raw materials.
MS: (M+H) 359.
H$^1$-NMR (DMSO, δ (ppm)): 0.97 (t, 3H), 1.49 (m, 2H), 1.81 (m, 2H), 4.03 (s, 3H), 4.24 (t, 2H), 7.50 (d, 2H), 7.58 (s, 1H), 7.91 (d, 3H), 9.64 (s, 1H).

Example 17

The Synthesis of 6-methoxy-7-n-butoxy-4-(3-trifluoromethylanilino)-benzo[d][1,2,3]triazine According to the synthesis method of Example 11, 3-trifluoromethyl-phenylamine instead of phenylamine was used as the raw materials.
MS: (M+H) 393.
H$^1$-NMR (DMSO, δ (ppm)): 0.97 (t, 3H), 1.49 (m, 2H), 1.81 (m, 2H), 4.04 (s, 3H), 4.24 (t, 2H), 7.50 (d, 1H), 7.60 (s, 1H), 7.71 (t, 1H), 7.90 (s, 1H), 8.29 (m, 2H), 9.77 (s, 1H).

Example 18

The Synthesis of 6-methoxy-7-n-butoxy-4-(4-trifluoromethylanilino)-benzo[d][1,2,3]triazine According to the synthesis method of Example 11, 4-trifluoromethyl phenylamine instead of phenylamine was used as the raw materials.
MS: (M+H) 393.
H$^1$-NMR (DMSO, δ (ppm)): 0.98 (t, 3H), 1.50 (m, 2H), 1.82 (m, 2H), 4.05 (s, 3H), 4.26 (t, 2H), 7.62 (s, 1H), 7.81 (d, 2H), 7.94 (s, 1H), 8.16 (d, 2H), 9.80 (s, 1H).

Example 19

The Synthesis of 6-methoxy-7-n-butoxy-4-(3-trifluoromethoxyanilino)-benzo[d][1,2,3]triazine According to the synthesis method of Example 11, 3-trifluoromethoxy-phenylamine instead of phenylamine was used as the raw materials.
MS: (M+H) 409.
H$^1$-NMR (DMSO, δ (ppm)): 0.97 (t, 3H), 1.49 (m, 2H), 1.81 (m, 2H), 4.04 (s, 3H), 4.25 (t, 2H), 7.15 (d, 1H), 7.57 (m, 2H), 7.93 (m, 2H), 8.01 (s, 1H), 9.74 (s, 1H).

Example 20

The Synthesis of 6-methoxy-7-n-butoxy-4-(4-trifluoromethoxyanilino)-benzo[d][1,2,3]triazine According to the synthesis method of Example 11, 4-trifluoromethoxy phenylamine instead of phenylamine was used as the raw materials.
MS: (M+H) 409.
H$^1$-NMR (DMSO, δ (ppm)): 0.97 (t, 3H), 1.49 (m, 2H), 1.81 (m, 2H), 4.04 (s, 3H), 4.25 (t, 2H), 7.46 (d, 2H), 7.58 (s, 1H), 7.90 (s, 1H), 7.98 (d, 2H), 9.69 (s, 1H).

Example 21

The Synthesis of 6-methoxy-7-n-butoxy-4-(3-chloroanilino)-benzo[d][1,2,3]triazine According to the synthesis method of Example 11, 3-chloro phenylamine instead of phenylamine was used as the raw materials.
MS: (M+H) 359.
H$^1$-NMR (DMSO, δ (ppm)): 0.97 (t, 3H), 1.49 (m, 2H), 1.81 (m, 2H), 4.04 (s, 3H), 4.25 (t, 2H), 7.21 (d, 1H), 7.47 (t, 1H), 7.59 (s, 1H), 7.86 (m, 2H), 8.10 (s, 1H), 9.64 (s, 1H).

Example 22

The Synthesis of 6-methoxy-7-n-butoxy-4-(3-chloro-4-fluoroanilino)-benzo[d][1,2,3]triazine According to the synthesis method of Example 11, 3-chloro-4-fluoro-phenylamine instead of phenylamine was used as the raw materials.
MS: (M+H) 377.
H$^1$-NMR (DMSO, δ (ppm)): 0.97 (t, 3H), 1.50 (m, 2H), 1.81 (m, 2H), 4.03 (s, 3H), 4.22 (t, 2H), 7.51 (m, 1H), 7.54 (s, 1H), 7.86 (m, 2H), 8.18 (d, 1H), 9.66 (s, 1H).

Example 23

The Synthesis of 6-methoxy-7-n-butoxy-4-(3-trifluoromethyl-4-fluoroanilino)-benzo[d][1,2,3]triazine According to the synthesis method of Example 11, 3-trifluoromethyl-4-fluoro phenylamine instead of phenylamine was used as the raw materials.

MS: (M+H) 411.

H$^1$-NMR (DMSO, δ (ppm)): 0.97 (t, 3H), 1.49 (m, 2H), 1.81 (m, 2H), 4.04 (s, 3H), 4.25 (t, 2H), 7.62 (m, 2H), 7.87 (s, 1H), 8.29 (m, 2H), 9.78 (s, 1H).

Example 24

The Synthesis of 6-methoxy-7-n-butoxy-4-(2-fluoroanilino)-benzo[d][1,2,3]triazine According to the synthesis method of Example 11, 2-fluoro phenylamine instead of phenylamine was used as the raw materials.

MS: (M+H) 343.

H$^1$-NMR (DMSO, δ (ppm)): 0.97 (t, 3H), 1.49 (m, 2H), 1.81 (m, 2H), 4.01 (s, 3H), 4.24 (t, 2H), 7.35 (m, 3H), 7.59 (m, 2H), 7.87 (s, 1H), 9.66 (s, 1H).

Example 25

The Synthesis of 6-methoxy-7-n-butoxy-4-(3-bromoanilino)-benzo[d][1,2,3]triazine According to the synthesis method of Example 11, 3-bromo phenylamine instead of phenylamine was used as the raw materials.

MS: (M+H) 403.

H$^1$-NMR (DMSO, δ (ppm)): 0.97 (t, 3H), 1.49 (m, 2H), 1.81 (m, 2H), 4.04 (s, 3H), 4.25 (t, 2H), 7.39 (m, 2H), 7.59 (s, 1H), 7.90 (m, 2H), 8.22 (s, 1H), 9.66 (s, 1H).

Example 26

The Synthesis of 6-methoxy-7-n-butoxy-4-(4-fluoroanilino)-benzo[d][1,2,3]triazine According to the synthesis method of Example 11, 4-fluoro phenylamine instead of phenylamine was used as the raw materials.

MS: (M+H) 343.

H$^1$-NMR (DMSO, δ (ppm)): 0.97 (t, 3H), 1.49 (m, 2H), 1.81 (m, 2H), 4.03 (s, 3H), 4.24 (t, 2H), 7.29 (t, 2H), 7.56 (s, 1H), 7.84 (m, 3H), 9.59 (s, 1H).

Example 27

The Synthesis of 6-methoxy-7-n-butoxy-4-(4-methylanilino)-benzo[d][1,2,3]triazine According to the synthesis method of Example 11, 4-methyl phenylamine instead of phenylamine was used as the raw materials.

MS: (M+H) 339.

H$^1$-NMR (DMSO, δ (ppm)): 0.97 (t, 3H), 1.49 (m, 2H), 1.81 (m, 2H), 4.02 (s, 3H), 4.24 (t, 2H), 7.25 (d, 2H), 7.54 (s, 1H), 7.70 (d, 2H), 7.90 (s, 1H), 9.51 (s, 1H).

Example 28

The Synthesis of 6-methoxy-7-ethoxy-4-anilino-benzo[d][1,2,3]triazine

According to the synthesis method of Example 11, ethyl bromide instead of butyl bromide was used as the raw materials.

MS: (M+H) 297.

H$^1$-NMR (DMSO, δ (ppm)): 1.44 (t, 3H), 4.03 (s, 3H), 4.31 (m, 2H), 7.18 (t, 1H), 7.45 (t, 2H), 7.55 (s, 1H), 7.83 (d, 2H), 7.92 (s, 1H), 9.59 (s, 1H).

Example 29

The Synthesis of 6-methoxy-7-ethoxy-4-(3-fluoro-4-bromoanilino)-benzo[d][1,2,3]triazine According to the synthesis method of Example 11, ethyl bromide instead of butyl bromide and 3-fluoro-4-bromo phenylamine instead of phenylamine were used as the raw materials.

MS: (M+H) 393.

H$^1$-NMR (DMSO, δ (ppm)): 1.44 (t, 3H), 4.04 (s, 3H), 4.31 (m, 2H), 7.59 (s, 1H), 7.72 (m, 2H), 7.89 (s, 1H), 8.14 (d, 1H), 9.74 (s, 1H).

Example 30

The Synthesis of 6-methoxy-7-ethoxy-4-(3,5-dichloroanilino)-benzo[d][1,2,3]triazine According to the synthesis method of Example 11, ethyl bromide instead of butyl bromide and 3,5-dichloro phenylamine instead of phenylamine were used as the raw materials.

MS: (M+H) 365.

H$^1$-NMR (DMSO, δ (ppm)): 1.44 (t, 3H), 4.05 (s, 3H), 4.31 (m, 2H), 7.36 (s, 1H), 7.62 (s, 1H), 7.88 (s, 1H), 8.10 (s, 1H), 9.71 (s, 1H).

Example 31

The Synthesis of 6-methoxy-7-ethoxy-4-(3,5-difluoroanilino)-benzo[d][1,2,3]triazine According to the synthesis method of Example 11, ethyl bromide instead of butyl bromide and 3,5-difluoro phenylamine instead of phenylamine were used as the raw materials.

MS: (M+H) 333.

H$^1$-NMR (DMSO, δ (ppm)): 1.45 (t, 3H), 4.05 (s, 3H), 4.31 (m, 2H), 7.00 (t, 1H), 7.62 (s, 1H), 7.75 (d, 2H), 7.88 (s, 1H), 9.75 (s, 1H).

Example 32

The Synthesis of 6-methoxy-7-ethoxy-4-(3,4-dichloroanilino)-benzo[d][1,2,3]triazine According to the synthesis method of Example 11, ethyl bromide instead of butyl bromide and 3,4-dichloro phenylamine instead of phenylamine were used as the raw materials.

MS: (M+H) 365.

H$^1$-NMR (DMSO, δ (ppm)): 1.44 (t, 3H), 4.04 (s, 3H), 4.31 (m, 2H), 7.60 (s, 1H), 7.70 (d, 1H), 7.91 (m, 2H), 8.31 (m, 1H), 9.71 (s, 1H).

Example 33

The Synthesis of 6-methoxy-7-ethoxy-4-(4-chloroanilino)-benzo[d][1,2,3]triazine

According to the synthesis method of Example 11, ethyl bromide instead of butyl bromide and 4-chloro phenylamine instead of phenylamine were used as the raw materials.

MS: (M+H) 331.
H$^1$-NMR (DMSO, δ (ppm)): 1.44 (t, 3H), 4.03 (s, 3H), 4.29 (m, 2H), 7.53 (m, 3H), 7.91 (m, 3H), 9.68 (s, 1H).

Example 34

The Synthesis of 6-methoxy-7-ethoxy-4-(3-trifluoromethylanilino)-benzo[d][1,2,3]triazine According to the synthesis method of Example 11, ethyl bromide instead of butyl bromide and 3-trifluoromethyl phenylamine instead of phenylamine were used as the raw materials.
MS: (M+H) 365.
H$^1$-NMR (DMSO, δ (ppm)): 1.45 (t, 3H), 4.05 (s, 3H), 4.31 (m, 2H), 7.52 (d, 1H), 7.60 (s, 1H), 7.69 (t, 1H), 7.92 (s, 1H), 8.29 (m, 2H), 9.78 (s, 1H).

Example 35

The Synthesis of 6-methoxy-7-ethoxy-4-(4-trifluoromethylanilino)-benzo[d][1,2,3]triazine According to the synthesis method of Example 11, ethyl bromide instead of butyl bromide and 4-trifluoromethyl phenylamine instead of phenylamine were used as the raw materials.
MS: (M+H) 365.
H$^1$-NMR (DMSO, δ (ppm)): 1.45 (t, 3H), 4.05 (s, 3H), 4.31 (m, 2H), 7.60 (s, 1H), 7.81 (d, 2H), 7.94 (s, 1H), 8.16 (d, 2H), 9.80 (s, 1H).

Example 36

The Synthesis of 6-methoxy-7-ethoxy-4-(3-trifluoromethoxyanilino)-1,2,3-benzotriazine According to the synthesis method of Example 11, ethyl bromide instead of butyl bromide and 3-trifluoromethoxy phenylamine instead of phenylamine were used as the raw materials.
MS: (M+H) 381.
H$^1$-NMR (DMSO, δ (ppm)): 1.45 (t, 3H), 4.05 (s, 3H), 4.31 (m, 2H), 7.15 (d, 1H), 7.57 (m, 2H), 7.93 (m, 2H), 8.04 (s, 1H), 9.73 (s, 1H).

Example 37

The Synthesis of 6-methoxy-7-ethoxy-4-(4-trifluoromethoxyanilino)-1,2,3-benzotriazine According to the synthesis method of Example 11, ethyl bromide instead of butyl bromide and 4-trifluoromethoxy phenylamine instead of phenylamine were used as the raw materials.
MS: (M+H) 409.
H$^1$-NMR (DMSO, δ (ppm)): 1.44 (t, 3H), 4.04 (s, 3H), 4.30 (m, 2H), 7.46 (d, 2H), 7.57 (s, 1H), 7.90 (s, 1H), 7.98 (d, 2H), 9.69 (s, 1H).

Example 38

The Synthesis of 6-methoxy-7-ethoxy-4-(3-chloroanilino)-benzo[d][1,2,3]triazine

According to the synthesis method of Example 11, ethyl bromide instead of butyl bromide and 4-chloro phenylamine instead of phenylamine were used as the raw materials.
MS: (M+H) 331.
H$^1$-NMR (DMSO, δ (ppm)): 1.44 (t, 3H), 4.04 (s, 3H), 4.30 (m, 2H), 7.21 (d, 1H), 7.47 (t, 1H), 7.59 (s, 1H), 7.84 (d, 1H), 7.90 (s, 1H), 8.09 (s, 1H), 9.65 (s, 1H).

Example 39

The Synthesis of 6-methoxy-7-ethoxy-4-(3-chloro-4-fluoroanilino)-benzo[d][1,2,3]triazine According to the synthesis method of Example 11, ethyl bromide instead of butyl bromide and 3-chloro-4-fluoro phenylamine instead of phenylamine were used as the raw materials.
MS: (M+H) 349.
H$^1$-NMR (DMSO, δ (ppm)): 1.44 (t, 3H), 4.03 (s, 3H), 4.30 (m, 2H), 7.51 (m, 1H), 7.54 (s, 1H), 7.81 (m, 1H), 7.87 (s, 1H), 8.18 (d, 1H), 9.66 (s, 1H).

Example 40

The Synthesis of 6-methoxy-7-ethoxy-4-(3-trifluoromethyl-4-fluoroanilino)-benzo[d][1,2,3]triazine According to the synthesis method of Example 11, ethyl bromide instead of butyl bromide and 3-trifluoromethyl-4-fluoro phenylamine instead of phenylamine were used as the raw materials.
MS: (M+H) 383.
H$^1$-NMR (DMSO, δ (ppm)): 1.44 (t, 3H), 4.04 (s, 3H), 4.31 (m, 2H), 7.60 (m, 2H), 7.88 (s, 1H), 8.28 (m, 2H), 9.79 (s, 1H).

Example 41

The Synthesis of 6-methoxy-7-ethoxy-4-(2-fluoroanilino)-benzo[d][1,2,3]triazine

According to the synthesis method of Example 11, ethyl bromide instead of butyl bromide and 2-fluoro phenylamine instead of phenylamine were used as the raw materials.
MS: (M+H) 315.
H$^1$-NMR (DMSO, δ (ppm)): 1.45 (t, 3H), 4.02 (s, 3H), 4.31 (m, 2H), 7.36 (m, 3H), 7.59 (m, 2H), 7.88 (s, 1H), 9.67 (s, 1H).

Example 42

The Synthesis of 6-methoxy-7-ethoxy-4-(3-bromoanilino)-benzo[d][1,2,3]triazine

According to the synthesis method of Example 11, ethyl bromide instead of butyl bromide and 3-bromo phenylamine instead of phenylamine were used as the raw materials.
MS: (M+H) 375.
H$^1$-NMR (DMSO, δ (ppm)): 1.44 (t, 3H), 4.04 (s, 3H), 4.31 (m, 2H), 7.39 (m, 2H), 7.58 (s, 1H), 7.90 (m, 2H), 8.21 (s, 1H), 9.64 (s, 1H).

Example 43

The Synthesis of 6-methoxy-7-ethoxy-4-(4-methylanilino)-benzo[d][1,2,3]triazine

According to the synthesis method of Example 11, ethyl bromide instead of butyl bromide and 4-methyl phenylamine instead of phenylamine were used as the raw materials. MS: (M+H) 311.

H$^1$-NMR (DMSO, δ (ppm)): 1.44 (t, 3H), 4.02 (s, 3H), 4.30 (m, 2H), 7.25 (d, 2H), 7.53 (s, 1H), 7.70 (d, 2H), 7.90 (s, 1H), 9.50 (s, 1H).

Example 44

The Synthesis of 6-methoxy-7-pentyloxy-4-anilino-benzo[d][1,2,3]triazine

According to the synthesis method of Example 11, pentyl bromide instead of butyl bromide was used as the raw materials.

MS: (M+H) 339.
H$^1$-NMR (DMSO, δ (ppm)): 0.92 (t, 3H), 1.39 (m, 4H), 1.82 (m, 2H), 4.03 (s, 3H), 4.23 (t, 2H), 7.18 (t, 1H), 7.45 (t, 2H), 7.56 (s, 1H), 7.83 (d, 2H), 7.92 (s, 1H), 9.59 (s, 1H).

Example 45

The Synthesis of 6-methoxy-7-pentyloxy-4-(3-fluoro-4-bromoanilino)-benzo[d][1,2,3]triazine According to the synthesis method of Example 11, pentyl bromide instead of butyl bromide and 3-fluoro-4-bromo phenylamine instead of phenylamine were used as the raw materials.

MS: (M+H) 435.
H$^1$-NMR (DMSO, δ (ppm)): 0.93 (t, 3H), 1.42 (m, 4H), 1.82 (m, 2H), 4.04 (s, 3H), 4.24 (t, 2H), 7.61 (s, 1H), 7.74 (m, 2H), 7.90 (s, 1H), 8.16 (d, 1H), 9.75 (s, 1H).

Example 46

The Synthesis of 6-methoxy-7-pentyloxy-4-(3,5-dichloroanilino)-benzo[d][1,2,3]triazine According to the synthesis method of Example 11, pentyl bromide instead of butyl bromide and 3,5-dichloro phenylamine instead of phenylamine were used as the raw materials.

MS: (M+H) 407.
H$^1$-NMR (DMSO, δ (ppm)): 0.93 (t, 3H), 1.41 (m, 4H), 1.82 (m, 2H), 4.03 (s, 3H), 4.24 (t, 2H), 7.36 (s, 1H), 7.61 (s, 1H), 7.88 (s, 1H), 8.09 (s, 1H), 9.72 (s, 1H).

Example 47

The Synthesis of 6-methoxy-7-pentyloxy-4-(3,5-difluoroanilino)-benzo[d][1,2,3]triazine According to the synthesis method of Example 11, pentyl bromide instead of butyl bromide and 3,5-difluoro phenylamine instead of phenylamine were used as the raw materials.

MS: (M+H) 375.
H$^1$-NMR (DMSO, δ (ppm)): 0.92 (t, 3H), 1.42 (m, 4H), 1.83 (m, 2H), 4.05 (s, 3H), 4.24 (t, 2H), 7.00 (t, 1H), 7.62 (s, 1H), 7.75 (d, 2H), 7.88 (s, 1H), 9.77 (s, 1H).

Example 48

The Synthesis of 6-methoxy-7-pentyloxy-4-(3,4-dichloroanilino)-benzo[d][1,2,3]triazine According to the synthesis method of Example 11, pentyl bromide instead of butyl bromide and 3,4-dichloro phenylamine instead of phenylamine were used as the raw materials.

MS: (M+H) 407.
H$^1$-NMR (DMSO, δ (ppm)): 0.92 (t, 3H), 1.42 (m, 4H), 1.82 (m, 2H), 4.04 (s, 3H), 4.24 (t, 2H), 7.60 (s, 1H), 7.70 (d, 1H), 7.91 (m, 2H), 8.31 (m, 1H), 9.71 (s, 1H).

Example 49

The Synthesis of 6-methoxy-7-pentyloxy-4-(4-chloroanilino)-benzo[d][1,2,3]triazine According to the synthesis method of Example 11, pentyl bromide instead of butyl bromide and 4-chloro phenylamine instead of henylamine were used as the raw materials.

MS: (M+H) 373.
H$^1$-NMR (DMSO, δ (ppm)): 0.92 (t, 3H), 1.42 (m, 4H), 1.81 (m, 2H), 4.03 (s, 3H), 4.24 (t, 2H), 7.53 (m, 3H), 7.91 (m, 3H), 9.63 (s, 1H).

Example 50

The Synthesis of 6-methoxy-7-pentyloxy-4-(3-trifluoromethylanilino)-benzo[d][1,2,3]triazine According to the synthesis method of Example 11, pentyl bromide instead of butyl bromide and 3-trifluoromethyl phenylamine instead of phenylamine were used as the raw materials.

MS: (M+H) 407.
H$^1$-NMR (DMSO, δ (ppm)): 0.93 (t, 3H), 1.43 (m, 4H), 1.84 (m, 2H), 4.06 (s, 3H), 4.25 (t, 2H), 7.52 (d, 1H), 7.61 (s, 1H), 7.70 (t, 1H), 7.92 (s, 1H), 8.30 (m, 2H), 9.79 (s, 1H).

Example 51

The Synthesis of 6-methoxy-7-pentyloxy-4-(4-trifluoromethylanilino)-benzo[d][1,2,3]triazine According to the synthesis method of Example 11, pentyl bromide instead of butyl bromide and 4-trifluoromethyl phenylamine instead of phenylamine were used as the raw materials.

MS: (M+H) 407.
H$^1$-NMR (DMSO, δ (ppm)): 0.92 (t, 3H), 1.42 (m, 4H), 1.83 (m, 2H), 4.05 (s, 3H), 4.25 (t, 2H), 7.61 (s, 1H), 7.81 (d, 2H), 7.93 (s, 1H), 8.16 (d, 2H), 9.81 (s, 1H).

Example 52

The Synthesis of 6-methoxy-7-pentyloxy-4-(3-trifluoromethoxyanilino)-benzo[d][1,2,3]triazine According to the synthesis method of Example 11, pentyl bromide instead of butyl bromide and 3-trifluoromethoxy phenylamine instead of phenylamine were used as the raw materials.

MS: (M+H) 423.
H$^1$-NMR (DMSO, δ (ppm)): 0.92 (t, 3H), 1.42 (m, 4H), 1.83 (m, 2H), 4.05 (s, 3H), 4.24 (t, 2H), 7.15 (d, 1H), 7.57 (m, 2H), 7.92 (m, 2H), 8.04 (s, 1H), 9.72 (s, 1H).

Example 53

The Synthesis of 6-methoxy-7-pentyloxy-4-(3-trifluoromethoxyanilino)-benzo[d][1,2,3]triazine According to the synthesis method of Example 11, pentyl bromide instead of butyl bromide and 3-trifluoromethoxy phenylamine instead of phenylamine were used as the raw materials.

MS: (M+H) 423.
H¹-NMR (DMSO, δ (ppm)): 0.92 (t, 3H), 1.42 (m, 4H), 1.83 (m, 2H), 4.04 (s, 3H), 4.24 (t, 2H), 7.46 (d, 2H), 7.58 (s, 1H), 7.90 (s, 1H), 7.98 (d, 2H), 9.69 (s, 1H).

Example 54

The Synthesis of 6-methoxy-7-pentyloxy-4-(3-chloroanilino)-benzo[d][1,2,3]triazine According to the synthesis method of Example 11, pentyl bromide instead of butyl bromide and 3-chloro phenylamine instead of phenylamine were used as the raw materials.
MS: (M+H) 373.
H¹-NMR (DMSO, δ (ppm)): 0.92 (t, 3H), 1.42 (m, 4H), 1.83 (m, 2H), 4.04 (s, 3H), 4.23 (t, 2H), 7.21 (d, 1H), 7.47 (t, 1H), 7.59 (s, 1H), 7.84 (d, 1H), 7.90 (s, 1H), 8.10 (s, 1H), 9.66 (s, 1H).

Example 55

The Synthesis of 6-methoxy-7-pentyloxy-4-(3-chloro-4-fluoroanilino)benzo[d][1,2,3]triazine According to the synthesis method of Example 11, pentyl bromide instead of butyl bromide and 3-chloro-4-fluoro phenylamine instead of phenylamine were used as the raw materials.
MS: (M+H) 391.
H¹-NMR (DMSO, δ (ppm)): 0.92 (t, 3H), 1.42 (m, 4H), 1.82 (m, 2H), 4.04 (s, 3H), 4.24 (t, 2H), 7.51 (d, 1H), 7.59 (s, 1H), 7.87 (d, 1H), 8.18 (s, 1H), 9.67 (s, 1H).

Example 56

The Synthesis of 6-methoxy-7-pentyloxy-4-(3-trifluoromethyl-4-fluoroanilino)-benzo[d][1,2,3]triazine According to the synthesis method of Example 11, pentyl bromide instead of butyl bromide and 3-trifluoromethyl-4-fluoro phenylamine instead of phenylamine were used as the raw materials.
MS: (M+H) 425.
H¹-NMR (DMSO, δ (ppm)): 0.92 (t, 3H), 1.42 (m, 4H), 1.83 (m, 2H), 4.04 (s, 3H), 4.24 (t, 2H), 7.60 (m, 2H), 7.88 (s, 1H), 8.29 (m, 2H), 9.78 (s, 1H).

Example 57

The Synthesis of 6-methoxy-7-pentyloxy-4-(2-fluoroanilino)-benzo[d][1,2,3]triazine According to the synthesis method of Example 11, pentyl bromide instead of butyl bromide and 2-fluoro phenylamine instead of phenylamine were used as the raw materials.
MS: (M+H) 357.
H¹-NMR (DMSO, δ (ppm)): 0.92 (t, 3H), 1.42 (m, 4H), 1.83 (m, 2H), 4.01 (s, 3H), 4.24 (t, 2H), 7.36 (m, 3H), 7.59 (m, 2H), 7.88 (s, 1H), 9.65 (s, 1H).

Example 58

The Synthesis of 6-methoxy-7-pentyloxy-4-(3-bromoanilino)-benzo[d][1,2,3]triazine According to the synthesis method of Example 11, pentyl bromide instead of butyl bromide and 3-bromo phenylamine instead of phenylamine were used as the raw materials.
MS: (M+H) 417.
H¹-NMR (DMSO, δ (ppm)): 0.92 (t, 3H), 1.42 (m, 4H), 1.82 (m, 2H), 4.04 (s, 3H), 4.24 (t, 2H), 7.39 (m, 2H), 7.59 (s, 1H), 7.91 (m, 2H), 8.21 (s, 1H), 9.63 (s, 1H).

Example 59

The Synthesis of 6-methoxy-7-pentyloxy-4-(4-fluoroanilino)-benzo[d][1,2,3]triazine According to the synthesis method of Example 11, pentyl bromide instead of butyl bromide and 4-fluoro phenylamine instead of phenylamine were used as the raw materials.
MS: (M+H) 357.
H¹-NMR (DMSO, δ (ppm)): 0.92 (t, 3H), 1.42 (m, 4H), 1.82 (m, 2H), 4.03 (s, 3H), 4.23 (t, 2H), 7.29 (t, 2H), 7.55 (s, 1H), 7.82 (m, 2H), 7.88 (s, 1H), 9.60 (s, 1H).

Example 60

The Synthesis of 6-methoxy-7-pentyloxy-4-(4-methylanilino)-benzo[d][1,2,3]triazine According to the synthesis method of Example 11, pentyl bromide instead of butyl bromide and 4-methyl phenylamine instead of phenylamine were used as the raw materials.
MS: (M+H) 353.
H¹-NMR (DMSO, δ (ppm)): 0.92 (t, 3H), 1.42 (m, 4H), 1.83 (m, 2H), 4.02 (s, 3H), 4.23 (t, 2H), 7.25 (d, 2H), 7.53 (s, 1H), 7.69 (d, 2H), 7.90 (s, 1H), 9.50 (s, 1H).

Example 61

The Synthesis of 6-methoxy-7-chloropropoxy-4-anilino-benzo[d][1,2,3]triazine

According to the synthesis method of Example 11, 1-bromo-3-chloropropane instead of butyl bromide was used as the raw materials.
MS: (M+H) 345.
H¹-NMR (DMSO, δ (ppm)): 2.29 (m, 2H), 3.84 (t, 2H), 4.04 (s, 3H), 4.37 (t, 2H), 7.18 (t, 1H), 7.45 (t, 2H), 7.60 (s, 1H), 7.83 (d, 2H), 7.94 (s, 1H), 9.59 (s, 1H).

Example 62

The Synthesis of 6-methoxy-7-chloropropoxy-4-(3-fluoro-4-bromoanilino)-benzo[1,2,3]triazine According to the synthesis method of Example 11, 1-bromo-3-chloropropane instead of butyl bromide and 3-fluoro-4-bromo phenylamine instead of phenylamine were used as the raw materials.
MS: (M+H) 443.
H¹-NMR (DMSO, δ (ppm)): 2.30 (m, 2H), 3.84 (t, 2H), 4.05 (s, 3H), 4.38 (t, 2H), 7.66 (s, 1H), 7.76 (m, 2H), 7.92 (s, 1H), 8.13 (d, 1H), 9.77 (s, 1H).

Example 63

The Synthesis of 6-methoxy-7-chloropropoxy-4-(3,5-dichloroanilino)-benzo[d][1,2,3]triazine According to the synthesis method of Example 11, 1-bromo-3-chloropropane instead of butyl bromide and 3,5-dichloro phenylamine instead of phenylamine were used as the raw materials.

MS: (M+H) 413.

H$^1$-NMR (DMSO, δ (ppm)): 2.30 (m, 2H), 3.84 (t, 2H), 4.06 (s, 3H), 4.39 (t, 2H), 7.37 (s, 1H), 7.68 (s, 1H), 7.91 (s, 1H), 8.10 (s, 1H), 9.74 (s, 1H).

Example 64

The Synthesis of 6-methoxy-7-chloropropoxy-4-(3, 5-difluoroanilino)-benzo[d][1,2,3]triazine According to the synthesis method of Example 11, 1-bromo-3-chloropropane instead of butyl bromide and 3,5-difluoro phenylamine instead of phenylamine were used as the raw materials.

MS: (M+H) 381.

H$^1$-NMR (DMSO, δ (ppm)): 2.30 (m, 2H), 3.84 (t, 2H), 4.06 (s, 3H), 4.39 (t, 2H), 7.00 (t, 1H), 7.68 (s, 1H), 7.75 (d, 2H), 7.92 (s, 1H), 9.80 (s, 1H).

Example 65

The Synthesis of 6-methoxy-7-chloropropoxy-4-(3, 4-dichloroanilino)-benzo[d][1,2,3]triazine According to the synthesis method of Example 11, 1-bromo-3-chloropropane instead of butyl bromide and 3,4-dichloro phenylamine instead of phenylamine were used as the raw materials.

MS: (M+H) 413.

H$^1$-NMR (DMSO, δ (ppm)): 2.30 (m, 2H), 3.84 (t, 2H), 4.05 (s, 3H), 4.38 (t, 2H), 7.66 (s, 1H), 7.71 (d, 1H), 7.91 (m, 2H), 8.31 (m, 1H), 9.74 (s, 1H).

Example 66

The Synthesis of 6-methoxy-7-chloropropoxy-4-(4-chloroanilino)-benzo[d][1,2,3]triazine According to the synthesis method of Example 11, 1-bromo-3-chloropropane instead of butyl bromide and 4-chloro phenylamine instead of phenylamine were used as the raw materials.

MS: (M+H) 379.

H$^1$-NMR (DMSO, δ (ppm)): 2.29 (m, 2H), 3.84 (t, 2H), 4.04 (s, 3H), 4.37 (t, 2H), 7.51 (d, 2H), 7.62 (s, 1H), 7.91 (m, 3H), 9.66 (s, 1H).

Example 67

The Synthesis of 6-methoxy-7-chloropropoxy-4-(3-trifluoromethylanilino)-benzo[d][1,2,3]triazine According to the synthesis method of Example 11, 1-bromo-3-chloropropane instead of butyl bromide and 3-trifluoromethyl phenylamine instead of phenylamine were used as the raw materials.

MS: (M+H) 413.

H$^1$-NMR (DMSO, δ (ppm)): 2.30 (m, 2H), 3.84 (t, 2H), 4.06 (s, 3H), 4.39 (t, 2H), 7.51 (d, 1H), 7.66 (s, 1H), 7.71 (t, 1H), 7.94 (s, 1H), 8.27 (m, 2H), 9.81 (s, 1H).

Example 68

The Synthesis of 6-methoxy-7-chloropropoxy-4-(4-trifluoromethylanilino)-benzo[d][1,2,3]triazine According to the synthesis method of Example 11, 1-bromo-3-chloropropane instead of butyl bromide and 4-trifluoromethyl phenylamine instead of phenylamine were used as the raw materials.

MS: (M+H) 413.

H$^1$-NMR (DMSO, δ (ppm)): 2.30 (m, 2H), 3.84 (t, 2H), 4.06 (s, 3H), 4.38 (t, 2H), 7.67 (s, 1H), 7.81 (d, 2H), 7.96 (s, 1H), 8.16 (d, 2H), 9.84 (s, 1H).

Example 69

The Synthesis of 6-methoxy-7-chloropropoxy-4-(3-trifluoromethoxyanilino)-benzo[d][1,2,3]triazine According to the synthesis method of Example 11, 1-bromo-3-chloropropane instead of butyl bromide and 3-trifluoromethoxy phenylamine instead of phenylamine were used as the raw materials.

MS: (M+H) 429.

H$^1$-NMR (DMSO, δ (ppm)): 2.30 (m, 2H), 3.84 (t, 2H), 4.06 (s, 3H), 4.38 (t, 2H), 7.15 (d, 1H), 7.57 (m, 2H), 7.92 (m, 2H), 8.05 (s, 1H), 9.75 (s, 1H).

Example 70

The Synthesis of 6-methoxy-7-chloropropoxy-4-(4-trifluoromethoxyanilino)-benzo[d][1,2,3]triazine According to the synthesis method of Example 11, 1-bromo-3-chloropropane instead of butyl bromide and 4-trifluoromethoxy phenylamine instead of phenylamine were used as the raw materials.

MS: (M+H) 429.

H$^1$-NMR (DMSO, δ (ppm)): 2.24 (m, 2H), 3.79 (t, 2H), 4.00 (s, 3H), 4.33 (t, 2H), 7.41 (d, 2H), 7.59 (s, 1H), 7.88 (s, 1H), 7.93 (d, 2H), 9.68 (s, 1H).

Example 71

The Synthesis of 6-methoxy-7-chloropropoxy-4-(3-chloroanilino)-benzo[d][1,2,3]triazine According to the synthesis method of Example 11, 1-bromo-3-chloropropane instead of butyl bromide and 3-chloro phenylamine instead of phenylamine were used as the raw materials.

MS: (M+H) 379.

H$^1$-NMR (DMSO, δ (ppm)): 2.32 (m, 2H), 3.70 (t, 2H), 4.05 (s, 3H), 4.38 (t, 2H), 7.22 (d, 1H), 7.47 (t, 1H), 7.64 (s, 1H), 7.85 (d, 1H), 7.93 (s, 1H), 8.10 (s, 1H), 9.69 (s, 1H).

Example 72

The Synthesis of 6-methoxy-7-chloropropoxy-4-(3-chloro-4-fluoroanilino)-benzo[d][1,2,3]triazine According to the synthesis method of Example 11, 1-bromo-3-chloropropane instead of butyl bromide and 3-chloro-4-fluoro phenylamine instead of phenylamine were used as the raw materials.

MS: (M+H) 397.

H$^1$-NMR (DMSO, δ (ppm)): 2.30 (m, 2H), 3.84 (t, 2H), 4.04 (s, 3H), 4.38 (t, 2H), 7.51 (t, 1H), 7.64 (s, 1H), 7.82 (m, 1H), 7.90 (s, 1H), 8.19 (d, 1H), 9.70 (s, 1H).

Example 73

The Synthesis of 6-methoxy-7-chloropropoxy-4-(3-trifluoromethyl-4-fluoroanilino)-benzo[d][1,2,3]triazine According to the synthesis method of Example 11, 1-bromo-3-chloropropane instead of butyl bromide and 3-trifluoromethyl-4-fluoro phenylamine instead of phenylamine were used as the raw materials.

MS: (M+H) 431.

H$^1$-NMR (DMSO, δ (ppm)): 2.30 (m, 2H), 3.84 (t, 2H), 4.05 (s, 3H), 4.38 (t, 2H), 7.62 (m, 2H), 7.91 (s, 1H), 8.29 (m, 2H), 9.82 (s, 1H).

Example 74

The Synthesis of 6-methoxy-7-chloropropoxy-4-(2-fluoroanilino)-benzo[d][1,2,3]triazine According to the synthesis method of Example 11, 1-bromo-3-chloropropane instead of butyl bromide and 2-fluoro phenylamine instead of phenylamine were used as the raw materials.

MS: (M+H) 363.

H$^1$-NMR (DMSO, δ (ppm)): 2.28 (m, 2H), 3.83 (t, 2H), 4.01 (s, 3H), 4.36 (t, 2H), 7.34 (m, 3H), 7.59 (m, 2H), 7.88 (s, 1H), 9.68 (s, 1H).

Example 75

The Synthesis of 6-methoxy-7-chloropropoxy-4-(3-bromoanilino)-benzo[d][1,2,3]triazine According to the synthesis method of Example 11, 1-bromo-3-chloropropane instead of butyl bromide and 3-bromo phenylamine instead of phenylamine were used as the raw materials.

MS: (M+H) 423.

H$^1$-NMR (DMSO, δ (ppm)): 2.30 (m, 2H), 3.84 (t, 2H), 4.05 (s, 3H), 4.38 (t, 2H), 7.40 (m, 2H), 7.64 (s, 1H), 7.93 (m, 2H), 8.22 (s, 1H), 9.68 (s, 1H).

Example 76

The Synthesis of 6-methoxy-7-chloropropoxy-4-(4-fluoroanilino)-benzo[d][1,2,3]triazine According to the synthesis method of Example 11, 1-bromo-3-chloropropane instead of butyl bromide and 4-fluoro phenylamine instead of phenylamine were used as the raw materials.

MS: (M+H) 363.

H$^1$-NMR (DMSO, δ (ppm)): 2.29 (m, 2H), 3.84 (t, 2H), 4.03 (s, 3H), 4.37 (t, 2H), 7.29 (t, 2H), 7.61 (s, 1H), 7.84 (m, 2H), 7.91 (s, 1H), 9.63 (s, 1H).

Example 77

The Synthesis of 6-methoxy-7-chloropropoxy-4-(4-methylanilino)-benzo[d][1,2,3]triazine According to the synthesis method of Example 11, 1-bromo-3-chloropropane instead of butyl bromide and 4-methyl phenylamine instead of phenylamine were used as the raw materials.

MS: (M+H) 359.

H$^1$-NMR (DMSO, δ (ppm)): 2.29 (m, 2H), 3.84 (t, 2H), 4.03 (s, 3H), 4.37 (t, 2H), 7.25 (d, 2H), 7.59 (s, 1H), 7.70 (d, 2H), 7.93 (s, 1H), 9.56 (s, 1H).

Example 78

The Synthesis of 6-chloro-4-anilino-pyrido[3,2-d][1,2,3]triazine

Step A: General Procedure for the Synthesis of 2-cyano-3-nitro-6-chloropyridine

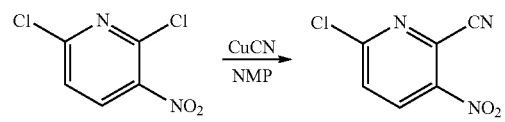

2,6-dichloro-3-nitropyridine (5 g, 26 mmol), Cuprous cyanide (4.64 g, 0.59 mml) and appropriate amount of N-methyl pyrrolidone were mixed to form a solution which was heated to 180° C. to react for 15 min, then cooled to 10° C. and poured into ice-water (200 mL) and stirred for 30 min. The solution was then filtered, washed with water and dried. A mixture of the filter cake and Toluene (50 mL) were stirred and heated under reflux for 10 min, then filtered while still hot. Repeated the above operation 3 times, and combined the filtrate. The filtrate was washed with water for 3 times, then with saturated sodium chloride solution for 1 time. The organic phase was dried with anhydrous magnesium sulfate and kept overnight. After filteration, the solution was evaporated under reduced pressure to dryness, and then filtered with a mixture of petroleum ether/aether (4:1) and air-dried to yield 1.78 g of orange yellow solid product with a recovery rate of 37.55%.

Step B: General Procedure for the Synthesis of 2-cyano-6-chloro-3-pyridinylamine

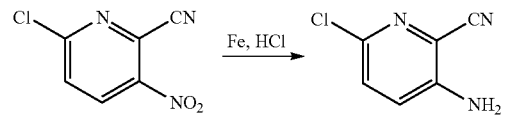

Added 4 g (21.8 mmol) of 2-cyano-3-nitro-6-chloropyridine into concentrated hydrochloric acid (15.00 mL) and ethanol (45.00 mL), then the solution was stirred thoroughly. 4.27 g (76.3 mmol) of reduced iron powder was added in batches to the mixture under a speed that maintained a slight boiling in the flask. The mixture was heated under reflux for 30 min, poured into ice-water (650 mL), stirred, and filtered. Sufficient aether was added to the filter cake and the mixture was stirred thoroughly and filtered. The filtrate was dried with anhydrous magnesium sulfate. The filtrate was adjusted to alkaline with concentrated ammonia first, then filtered and extracted with ether for 3 times. The combined solution of the organic phase and ether solution was dried with anhydrous magnesium sulfate before combined, and then filtered and evaporated under reduced pressure to yield 2.92 g of yellow solid product with a recovery rate of 87.42%.

Step C: General Procedure for the Synthesis of 1-phenyl-3-(2-cyano-6-chloro-3-pyridyl)triazene

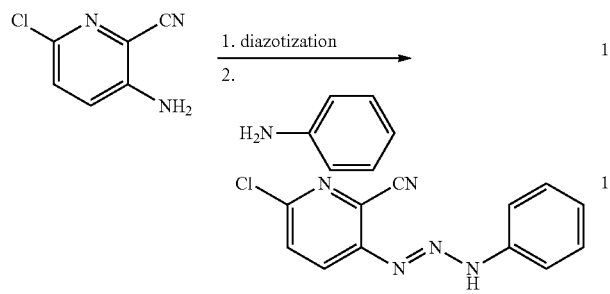

2-cyano-6-chloro-3-pyridinylamine (0.153 g, 1 mmol) was added into 3 mL of hydrochloric acid (10 mol/L), and then cooled to 0° C. in ice-salt bath. Sodium nitrite (0.072 g) dissolved in water (1.0 mL) was added to the solution dropwise under stirring for 20 min. The diazonium solution was neutralized with 0.093 g of aniline (1.0 mmol) dissolved in anhydrous ethanol to pH 5-6 and stirred for 2 h at 0-5° C. The solution was kept overnight, filtered, and washed with water till colorless to yield the crude product. The crude product was purified on a silica gel column with petroleum ether:ethylacetate (v/v)=20:1 to yield yellow solid product (0.116 g) with a recovery rate of 45.1%.

Step D: General Procedure for the Synthesis of 6-chloro-4-anilino-pyrido[3,2-d][1,2,3]triazine

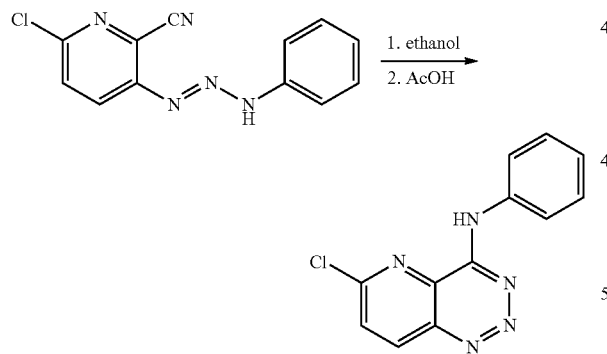

1-phenyl-3-(2-cyano-4-methoxy-5-n-butoxyphenyl)triazene (0.116 g, 0.45 mmol) was boiled in 70% ethanol (30.0 mL) for 1 h, and then the solution was evaporated under reduced pressure to dryness. Acetic acid (20.0 mL) was added to the solution, and then refluxed for 1 h, filtered, and washed with water till colorless. The filter cake was recrystallized in ethanol to yield light brown solid product (0.108 g) with a recovery rate of 93.1%.

MS: (M+H) 258.

$H^1$-NMR (DMSO, δ (ppm)): 7.22 (t, 1H), 7.45 (t, 2H), 8.00 (d, 2H), 8.19 (d, 1H), 8.66 (d, 1H), 10.36 (s, 1H).

Examples 79-93 were synthesised according to the synthesis method of Example 78 by choosing appropriate materials.

Example 79

The Synthesis of 6-chloro-4-(3-fluoro-4-bromoanilino)-pyrido[3,2-d][1,2,3]-triazine According to the synthesis method of Example 78, 4-bromo-3-fluoroaniline instead of aniline was used as the raw materials.

MS: (M+H) 354.

$H^1$-NMR (DMSO, δ (ppm)): 7.78 (t, 1H), 7.96 (d, 1H), 8.23 (d, 2H), 8.72 (d, 1H), 10.63 (s, 1H).

Example 80

The Synthesis of 6-chloro-4-(3,5-dichloroanilino)pyrido[3,2-d][1,2,3]triazine

According to the synthesis method of Example 78, 3,5-dichloroaniline instead of aniline was used as the raw materials.

MS: (M+Na) 350.

$H^1$-NMR (DMSO, δ (ppm)): 7.43 (s, 1H), 8.24 (d, 1H), 8.28 (s, 2H), 8.74 (d, 1H), 10.65 (s, 1H).

Example 81

The Synthesis of 6-chloro-4-(3,5-difluoroanilino)pyrido[3,2-d][1,2,3]triazine

According to the synthesis method of Example 78, 3,5-difluoroaniline instead of aniline was used as the raw materials.

MS: (M+H) 294.

$H^1$-NMR (DMSO, δ (ppm)): 7.06 (t, 1H), 7.97 (d, 2H), 8.24 (d, 1H), 8.73 (d, 1H), 10.65 (s, 1H).

Example 82

The Synthesis of 6-chloro-4-(3,4-dichloroanilino)pyrido[3,2-d][1,2,3]triazine

According to the synthesis method of Example 78, 3,4-dichloroaniline instead of aniline was used as the raw materials.

MS: (M+Na) 350.

$H^1$-NMR (DMSO, δ (ppm)): 7.72 (d, 1H), 8.11 (dd, 1H), 8.23 (d, 1H), 8.46 (d, 1H), 8.72 (d, 1H), 10.62 (s, 1H).

Example 83

The Synthesis of 6-chloro-4-(4-chloroanilino)pyrido[3,2][1,2,3]triazine

According to the synthesis method of Example 78, 4-chloroaniline instead of aniline was used as the raw materials.

MS: (M+Na) 314.

$H^1$-NMR (DMSO, δ (ppm)): 7.51 (d, 2H), 8.07 (d, 2H), 8.20 (d, 1H), 8.68 (d, 1H), 10.49 (s, 1H).

Example 84

The Synthesis of 6-chloro-4-(3-trifluoromethylanilino)pyrido[3,2-d][1,2,3]triazine According to the synthesis method of Example 78, 3-(trifluoromethyl)aniline instead of aniline was used as the raw materials.

MS: (M+Na) 348.

H$^1$-NMR (DMSO, δ (ppm)): 7.56 (d, 1H), 7.70 (t, 1H), 8.23 (d, 1H), 8.38 (d, 1H), 8.52 (s, 1H), 8.72 (d, 1H), 10.66 (s, 1H).

Example 85

The Synthesis of 6-chloro-4-(4-trifluoromethylanilino)pyrido[3,2-d][1,2,3]triazine According to the synthesis method of Example 78, 4-(trifluoromethyl)aniline instead of aniline was used as the raw materials.

MS: (M+Na) 348.

H$^1$-NMR (DMSO, δ (ppm)): 7.82 (d, 2H), 8.22 (d, 1H), 8.32 (d, 2H), 8.72 (d, 1H), 10.66 (s, 1H).

Example 86

The Synthesis of 6-chloro-4-(3-trifluoromethoxyanilino)pyrido[3,2-d][1,2,3]triazine According to the synthesis method of Example 78, 3-(trifluoromethoxy)aniline instead of aniline was used as the raw materials.

MS: (M+Na) 364.

H$^1$-NMR (DMSO, δ (ppm)): 7.19 (d, 1H), 7.58 (t, 1H), 8.15 (d, 1H), 8.22 (d, 2H), 8.71 (d, 1H), 10.61 (s, 1H).

Example 87

The Synthesis of 6-chloro-4-(4-trifluoromethoxyanilino)pyrido[3,2-d][1,2,3]triazine According to the synthesis method of Example 78, 4-(trifluoromethoxy)aniline instead of aniline was used as the raw materials.

MS: (M+Na) 364.

H$^1$-NMR (DMSO, δ (ppm)): 7.46 (d, 2H), 8.13 (d, 2H), 8.21 (d, 12H), 8.69 (d, 1H), 10.56 (s, 1H).

Example 88

The Synthesis of 6-chloro-4-(3-chloroanilino)pyrido[3,2-d][1,2,3]triazine

According to the synthesis method of Example 78, 3-chloroaniline instead of aniline was used as the raw materials.

MS: (M+Na) 314.

H$^1$-NMR (DMSO, δ (ppm)): 7.27 (d, 1H), 7.48 (t, 1H), 8.01 (d, 1H), 8.23 (m, 2H), 8.70 (d, 1H), 10.52 (s, 1H).

Example 89

The Synthesis of 6-chloro-4-(3-chloro-4-fluoroanilino)pyrido[3,2-d][1,2,3]triazine According to the synthesis method of Example 78, 3-chloro-4-fluoroaniline instead of aniline was used as the raw materials.

MS: (M+Na) 332.

H$^1$-NMR (DMSO, δ (ppm)): 7.52 (t, 1H), 8.01 (m, 1H), 8.21 (d, 1H), 8.33 (m, 1H), 8.70 (d, 1H), 10.56 (s, 1H).

Example 90

The Synthesis of 6-chloro-4-(3-trifluoromethyl-4-fluoroanilino)pyrido[3,2-d][1,2,3]-triazine According to the synthesis method of Example 78, 3-trifluoromethyl-4-fluoroaniline instead of aniline was used as the raw materials.

MS: (M+Na) 366.

H$^1$-NMR (DMSO, δ (ppm)): 7.62 (t, 1H), 8.21 (d, 1H), 8.42 (m, 1H), 8.50 (m, 1H), 8.70 (d, 1H), 10.69 (s, 1H).

Example 91

The Synthesis of 6-chloro-4-(2-fluoroanilino)pyrido[3,2-d][1,2,3]triazine

According to the synthesis method of Example 78, 2-fluoroaniline instead of aniline was used as the raw materials.

MS: (M+Na) 298.

H$^1$-NMR (DMSO, δ (ppm)): 7.36 (m, 3H), 7.71 (t, 1H), 8.21 (d, 1H), 8.68 (d, 1H), 10.36 (s, 1H).

Example 92

The Synthesis of 6-chloro-4-(3-bromoanilino)-pyrido[3,2-d][1,2,3]triazine

According to the synthesis method of Example 78, 3-bromoaniline instead of aniline was used as the raw materials.

MS: (M+Na) 358.

H$^1$-NMR (DMSO, δ (ppm)): 7.42 (m, 2H), 8.05 (m, 1H), 8.21 (d, 1H), 8.38 (s, 1H), 8.70 (d, 1H), 10.50 (s, 1H).

Example 93

The Synthesis of 6-chloro-4-(4-fluoroanilino)pyrido[3,2-d][1,2,3]triazine

According to the synthesis method of Example 78, 4-fluoroaniline instead of aniline was used as the raw materials.

MS: (M+Na) 298.

H$^1$-NMR (DMSO, δ (ppm)): 7.30 (t, 2H), 8.00 (m, 2H), 8.19 (d, 1H), 8.66 (d, 1H), 10.46 (s, 1H).

Example 94

The Synthesis of 6-methoxy-7-(3-morpholinopropoxy)-4-(3-chloro-4-fluoro anilino)-benzo[d][1,2,3]triazine Step A: General Procedure for the Synthesis of 3-methoxy-4-chloropropoxybenzonitrile

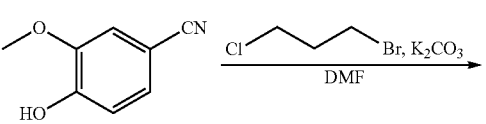

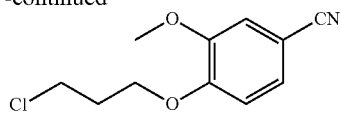

2-methoxy-4-cyano-phenol (0.25 g, 1.67 mmol) and anhydrous DMF (2.00 mL) were added into a round bottom flask. The solution was stirred and cooled in a water bath. Several batches of anhydrous K$_2$CO$_3$ (0.347 g, 2.50 mmol) were added to the solution and the mixture was stirred at 20° C. to react for 1 h. 1-chloro-3-bromopropane (0.23 ml, 2.14 mmol) was added, and the mixture was stirred at room temperature (25° C.) to react overnight. The mixture was heated to 37° C. to react for 6 h and then poured into a mixture of ice/H$_2$O (25 mL). After stirring for 10 min, a precipitate was formed. Filtered, washed with H$_2$O, and air-dried to yield white solid product (0.388 g) with a recovery rate of 90%.

Step B: General Procedure for the Synthesis of 2-nitro-4-chloropropoxy-5-methoxy-benzonitrile

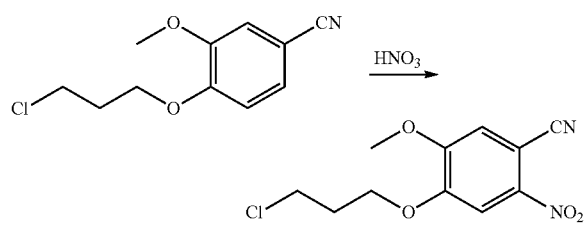

3-methoxy-4-chloropropoxybenzonitrile (1.350 g, 6 mmol) and nitric acid (6 mL) were added into a round bottom flask. The solution was heated to 30° C. while stirring to react for 2 h, then poured into ice-water, filtered, washed with water and air-dried to yield light yellow solid product (1.555 g) with a recovery rate of 96%.

Step C: General Procedure for the Synthesis of 2-amino-4-chloropropoxy-5-methoxy benzonitrile

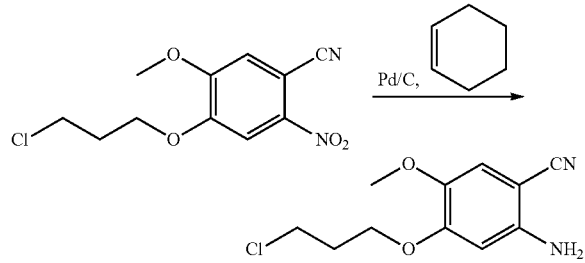

A mixture of 2-nitro-4-chloropropoxy-5-methoxy-benzonitrile (0.563 g, 2.24 mmol), Pd/C (0.035 g) and anhydrous ethanol (25.0 mL) were added into a round bottom flask. The solution was stirred and heated under reflux. Cyclohexene (1.15 mL) was added and refluxed until the disappearance of the starting materials as monitored by TLC. After cooling, the resulting mixture was filtered and washed with ethanol. The filtrate was concentrated to yield a solid product. The crude product was suspended in anhydrous ethanol (4 ml), stirred at 40° C. to react for 30 min, then cooled to room temperature, filtered and air-dried to yield light yellow solid product (0.352 g) with a recovery rate of 71%.

Step D: General Procedure for the Synthesis of 2-amino-4-(3-morpholinopropoxy)-5-methoxy benzonitrile

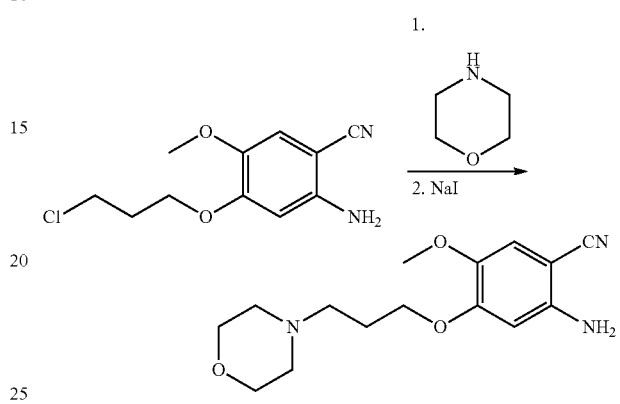

A mixture of 2-amino-4-chloropropoxy-5-methoxy-benzonitrile (1.000 g, 4.12 mmol), morpholine (1.0 mL) and catalytic amount of sodium iodide were added into a round bottom flask. The solution was stirred and heated under reflux for 2 h. After reaction, extracted the solution with dichloromethane and water, and then combined the organic phases. After evaporating most of the solvent, equivalent amount of hydrochloric acid ether was added into the solution, and filtered to yield 1.100 g of white solid product with a recovery rate of 91%.

Step E: General Procedure for the Synthesis of 1-(3-chloro-4-fluoroanilino)-3-(2-cyano-4-methoxy-5-(3-morpholinopropoxy)triazene

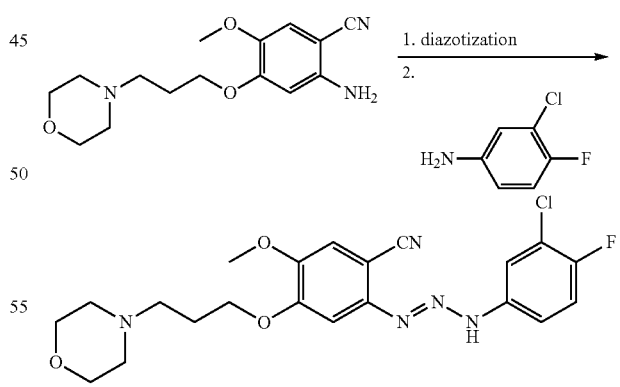

2-amino-4-(3-morpholinopropoxy)-5-methoxybenzonitrile (0.291 g, 1 mmol) was added into 3 mL of hydrochloric acid (10 mol/L) and cooled to 0° C. in ice salt bath. Sodium nitrite (0.072 g, 1 mmol) dissolved in water (1.0 mL) was added dropwise, and the mixture was stirred to react for 20 min. After adjusting the pH to 5~6 with sodium acetate, added dropwise 0.145 g of 3-chloro-4-fluoro phenylamine (1 mmol) dissolved in ethanol to the solution, stirred and reacted for 2 h, while keeping at pH 7 with sodium acetate under 0~5° C. The solution was kept overnight, and then filtered to yield the crude yellow product (0.405 g) with a recovery rate of 90.8%.

Step F: General Procedure for the Synthesis of 6-methoxy-7-(3-morpholino-propoxy)-4-(3-chloro-4-fluoroanilino)-benzo[d][1,2,3]triazine hydrochloride

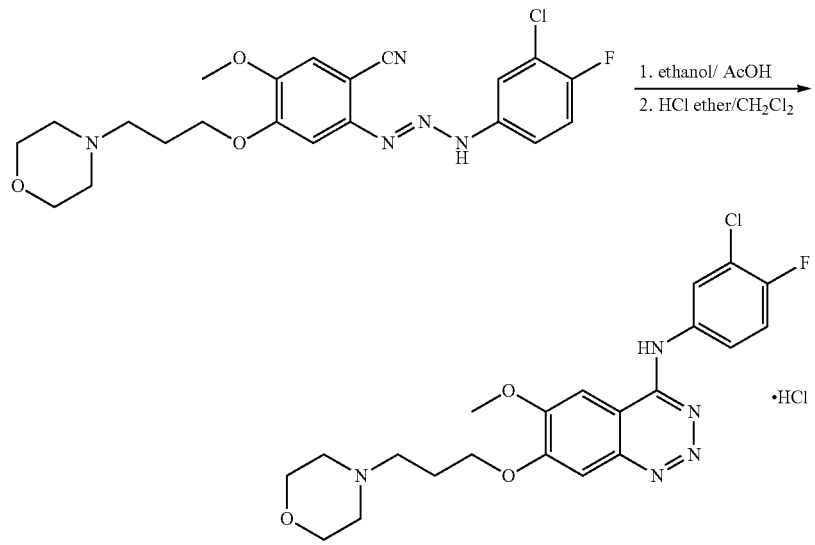

1-(3-chloro-4-fluoroanilino)-3-(2-cyano-4-methoxy-5-(3-morpholinopropoxy)triazene (0.405 g, 0.9 mmol) was added into 70% ethanol (25.0 mL). The solution was stirred and heated under reflux to react for 1.5 h then evaporated under reduced pressure. Glacial acetic acid (20.0 mL) was added steam dried solid product, and heated to boil to react for 1 h. Then the mixture was poured into ice-water and neutralized to pH 7 with saturated sodium hydroxide solution. Extracted the solution with ethyl acetate, combined the organic phased and dried overnight. After filteration, 0.5 g of gel silica was added, evaporated under reduced pressure to yield the crude column chromatography product. The crude product was first purified on a silica gel column with dichloromethane:methanol (v/v) =100:5 as the eluting agent, then purified by TLC with dichloromethane:methanol (v/v)=100:10 as the developing solvent, and the product was dissolved in dichloromethane with equivalent hydrochloric acid ether solution to yield orange yellow crystal product (0.133 g) with a recovery rate of 30.5%.

MS: (M+H) 448.

H$^1$-NMR (DMSO, δ (ppm)): 11.21 (s, 1H), 10.72 (s, 1H), 8.37 (s, 1H), 8.26 (m, 1H), 7.96 (m, 1H), 7.64 (s, 1H), 7.51 (t, 1H), 4.38 (t, 2H), 4.08 (s, 3H), 3.98 (d, 2H), 3.85 (t, 2H), 3.50 (d, 2H), 3.30 (s, 2H), 3.12 (d, 2H), 2.35 (s, 2H).

Examples 95-111 were synthesised according to the synthesis method of Example 94 by choosing appropriate materials.

Example 95

The Synthesis of 6-methoxy-7-(3-(piperidin-1-yl)-propoxy)-4-(3-chloro-4-fluoroanilino)-benzo[d][1,2,3]triazine hydrochloride According to the synthesis method of Example 94, piperidine instead of morpholine was used as the raw materials.

MS: (M+H) 446.

H$^1$-NMR (DMSO, δ (ppm)): 10.70 (s, 1H), 10.39 (s, 1H), 8.38 (s, 1H), 8.27 (m, 1H), 7.97 (m, 1H), 7.63 (s, 1H), 7.50 (t, 1H), 4.36 (d, 2H), 4.08 (t, 3H), 3.48 (d, 2H), 3.18 (m, 2H), 2.91 (m, 2H), 2.33 (d, 2H), 1.80 (m, 5H), 1.40 (m, 1H).

Example 96

The Synthesis of 6-methoxy-7-(3-N-methylpiperazin-1-yl-propoxy)-4-(3-chloro-4-fluoroanilino)-benzo[d][1,2,3]triazin-4-amine hydrochloride According to the synthesis method of Example 94, N-methyl piperazine instead of morpholine was used as the raw materials.

MS: (M+H) 461.

H$^1$-NMR (DMSO, δ (ppm)): 12.01 (s, 1H), 10.64 (s, 1H), 8.34 (s, 1H), 8.24 (m, 1H), 7.93 (t, 1H), 7.60 (s, 1H), 7.47 (t, 1H), 4.36 (t, 2H), 4.06 (s, 3H), 3.84 (s, 2H), 3.69 (s, 2H), 3.47 (s, 4H), 3.34 (s, 2H), 2.82 (s, 3H), 2.33 (s, 2H).

Example 97

The Synthesis of 6-methoxy-7-(3-imidazol-1-yl-propoxy)-4-(3-chloro-4-fluoroanilino)-benzo[d][1,2,3]triazine hydrochloride According to the synthesis method of Example 94, imidazole instead of morpholine was used as the raw materials.

MS: (M+H) 429.

H$^1$-NMR (DMSO, δ (ppm)): 14.73 (s, 1H), 10.85 (s, 1H), 9.23 (s, 1H), 8.44 (s, 1H), 8.30 (m, 1H), 8.00 (m, 1H), 7.86 (s, 1H), 7.77 (s, 1H), 7.61 (s, 1H), 7.50 (t, 1H), 4.44 (t, 2H), 4.35 (t, 2H), 4.07 (s, 3H), 2.44 (t, 2H).

Example 98

The Synthesis of 6-methoxy-7-(3-morpholinopropoxy)-4-(3-trifluoromethylanilino)benzo[d][1,2,3]triazine hydrochloride According to the synthesis method of Example 94, 3-trifluoromethyl aniline instead of 3-chloro-4-fluoroaniline was used as the raw materials.
MS: (M+H) 464.
H$^1$-NMR (DMSO, δ (ppm)): 11.15 (s, 1H), 10.52 (s, HA 8.42 (s, 1H), 8.33 (t, 2H), 7.67 (m, 2H), 7.51 (d, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 99

The Synthesis of 6-methoxy-7-(3-morpholinopropoxy)-4-(4-trifluoromethylanilino)benzo[d][1,2,3]triazine hydrochloride According to the synthesis method of Example 94, 4-trifluoromethyl aniline instead of 3-chloro-4-fluoroaniline was used as the raw materials.
MS: (M+H) 464.
H$^1$-NMR (DMSO, δ (ppm)): 11.58 (s, 1H), 10.70 (s, 1H), 8.48 (s, 1H), 8.33 (d, 2H), 7.78 (d, 2H), 7.64 (s, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 100

The Synthesis of 6-methoxy-7-(3-morpholino-propoxy)-4-(3-fluoro-4-bromoanilino)-benzo[d][1,2,3]triazine hydrochloride According to the synthesis method of Example 94, 3-fluoro-4-bromo aniline instead of 3-chloro-4-fluoroaniline was used as the raw materials.
MS: (M+H) 492.
H$^1$-NMR (DMSO, δ (ppm)): 11.30 (s, 1H), 10.53 (s, 1H), 8.40 (s, 1H), 8.30 (d, 1H), 7.94 (d, 1H), 7.73 (t, 1H), 7.64 (s, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 101

The Synthesis of 6-methoxy-7-(3-morpholinopropoxy)-4-(3,5-difluorophenyl)-benzo[d][1,2,3]triazine hydrochloride According to the synthesis method of Example 94, 3,5-difluoro aniline instead of 3-chloro-4-fluoroaniline was used as the raw materials.
MS: (M+H) 432.
H$^1$-NMR (DMSO, δ (ppm)): 11.30 (s, 1H), 10.53 (s, 1H), 8.63 (s, 1H), 8.08 (d, 2H), 7.65 (s, 1H), 6.98 (t, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 102

The Synthesis of 6-methoxy-7-(3-morpholinopropoxy)-4-(3-trifluoromethyl-4-fluoroanilino)-benzo[d][1,2,3]triazine hydrochloride According to the synthesis method of Example 94, 3-trifluoromethyl-4-fluoroaniline instead of 3-chloro-4-fluoroaniline was used as the raw materials.
MS: (M+H) 482.
H$^1$-NMR (DMSO, δ (ppm)): 11.17 (s, 1H), 10.58 (s, 1H), 8.47 (d, 1H), 8.40 (t, 1H), 8.34 (s, 1H), 7.64 (s, 1H), 7.60 (t, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 103

The Synthesis of 6-methoxy-7-(3-morpholinopropoxy)-4-(3-trifluoromethoxyanilino)benzo[d][1,2,3]triazine hydrochloride According to the synthesis method of Example 94, 3-trifluoromethoxy aniline instead of 3-chloro-4-fluoroaniline was used as the raw materials.
MS: (M+H) 480.
H$^1$-NMR (DMSO, δ (ppm)): 11.31 (s, 1H), 10.74 (s, 1H), 8.41 (s, 1H), 8.14 (s, 1H), 8.05 (t, 1H), 7.66 (s, 1H), 7.58 (t, 1H), 7.17 (d, 1H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 104

The Synthesis of 6-methoxy-7-(3-morpholinopropoxy)-4-(4-trifluoro methoxy-anilino)benzo[d][1,2,3]triazine hydrochloride According to the synthesis method of Example 94, 4-trifluoromethoxy aniline instead of 3-chloro-4-fluoroaniline was used as the raw materials.
MS: (M+H) 480.
H$^1$-NMR (DMSO, δ (ppm)): 11.38 (s, 1H), 10.83 (s, 1H), 8.44 (s, 1H), 8.06 (d, 2H), 7.64 (s, 1H), 7.46 (d, 2H), 4.38 (t, 2H), 4.09 (s, 3H), 3.98 (d, 2H), 3.85 (t, 2H), 3.50 (d, 2H), 3.30 (s, 2H), 3.12 (m, 2H), 2.35 (t, 2H).

Example 105

The Synthesis of 6-methoxy-7-(3-(piperidin-1-yl)propoxy)-4-(3-trifluoromethylanilino)benzo[d][1,2,3]triazine hydrochloride According to the synthesis method of Example 94, piperidine instead of morpholine and 3-trifluoromethyl aniline instead of 3-chloro-4-fluoroaniline were used as the raw materials.
MS: (M+H) 462.
H$^1$-NMR (DMSO, δ (ppm)): 10.58 (s, 1H), 10.41 (s, 1H), 8.44 (s, 1H), 8.35 (d, 2H), 7.68 (t, 1H), 7.65 (s, 1H), 7.52 (d, 1H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 106

The Synthesis of 6-methoxy-7-(3-(piperidin-1-yl)propoxy)-N-(4-trifluoromethylanilino)benzo[d][1,2,3]triazine hydrochloride According to the synthesis method of Example 94, piperidine instead of morpholine and 4-trifluoromethyl aniline instead of 3-chloro-4-fluoroaniline were used as the raw materials.
MS: (M+H) 462.
H$^1$-NMR (DMSO, δ (ppm)): 10.84 (s, 1H), 10.67 (s, 1H), 8.49 (s, 1H), 8.29 (d, 2H), 7.80 (d, 2H), 7.66 (s, 1H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 107

The Synthesis of 6-methoxy-7-(3-(piperidin-1-yl)-propoxy)-4-(3-fluoro-4-bromoanilino)-benzo[d][1,2,3]triazine hydrochloride According to the synthesis method of Example 94, piperidine instead of morpholine and 3-fluoro-4-chloroaniline instead of 3-chloro-4-fluoroaniline were used as the raw materials.
MS: (M+H) 490.
$H^1$-NMR (DMSO, δ (ppm)): 10.11 (s, 1H), 9.76 (s, 1H), 8.24 (d, 1H), 8.14 (s, 1H), 7.80 (m, 1H), 7.75 (t, 1H), 7.65 (s, 1H), 4.38 (t, 2H), 4.07 (s, 3H), 3.49 (d, 2H), 3.21 (m, 2H), 3.17 (s, 2H), 2.91 (m, 2H), 2.29 (m, 2H), 1.82 (d, 2H), 1.75 (m, 3H), 1.40 (m, 1H).

Example 108

The Synthesis of 6-methoxy-7-(3-(piperidin-1-yl)propoxy)-4-(3,5-difluoroanilino)-benzo[d][1,2,3]triazine hydrochloride According to the synthesis method of Example 94, piperidine instead of morpholine and 3,5-difluoro aniline instead of 3-chloro-4-fluoroaniline were used as the raw materials.
MS: (M+H) 430.
$H^1$-NMR (DMSO, δ (ppm)): 10.95 (s, 1H), 10.80 (s, 1H), 8.63 (s, 1H), 8.08 (d, 2H), 7.65 (s, 1H), 7.98 (t, 1H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 109

The Synthesis of 6-methoxy-7-(3-(piperidin-1-yl)propoxy)-4-(3-trifluoromethyl-4-fluoroanilino)-benzo[d][1,2,3]triazine hydrochloride According to the synthesis method of Example 94, piperidine instead of morpholine and 3-trifluoromethyl-4-fluoroaniline instead of 3-chloro-4-fluoroaniline were used as the raw materials.
MS: (M+H) 480.
$H^1$-NMR (DMSO, δ (ppm)): 10.93 (s, 1H), 10.40 (s, 1H), 8.46 (m, 1H), 8.38 (d, 2H), 7.64 (s, 1H), 7.60 (t, 1H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 110

The Synthesis of 6-methoxy-7-(3-(piperidin-1-yl)propoxy)-4-(3-trifluoromethoxyanilino)benzo[d][1,2,3]triazine hydrochloride According to the synthesis method of Example 94, piperidine instead of morpholine and 3-trifluoromethoxy aniline instead of 3-chloro-4-fluoroaniline were used as the raw materials.
MS: (M+H) 478.
$H^1$-NMR (DMSO, δ (ppm)): 11.03 (s, 1H), 10.69 (s, 1H), 8.53 (s, 1H), 8.16 (s, 1H), 8.06 (t, 1H), 7.65 (s, 1H), 7.57 (t, 1H), 7.19 (d, 1H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 111

The Synthesis of 6-methoxy-7-(3-(piperidin-1-yl)propoxy)-4-(4-trifluoromethoxyanilino)benzo[d][1,2,3]triazine hydrochloride According to the synthesis method of Example 94, piperidine instead of morpholine and 4-trifluoromethoxy aniline instead of 3-chloro-4-fluoroaniline were used as the raw materials.
MS: (M+H) 478.
$H^1$-NMR (DMSO, δ (ppm)): 10.83 (s, 1H), 10.55 (s, 1H), 8.40 (s, 1H), 8.05 (d, 2H), 7.64 (s, 1H), 7.46 (d, 2H), 4.38 (t, 2H), 4.35 (s, 3H), 3.49 (d, 2H), 3.21 (m, 2H), 2.91 (m, 2H), 2.33 (m, 2H), 1.81 (m, 4H), 1.71 (d, 1H), 1.41 (m, 1H).

Example 112

Pharmacological Research on the Present Invention

In Vitro Anti-Tumor Activity Test
1) Cell Resuscitation
Took the cells from liquid nitrogen carefully (cryopreserved pipe), and put the cells in 37° C. water bath right away to melt the crypopreservation medium to have the cells quickly pass through the temperature zone of 0 to 5° C., which would significantly impair the cells. Put cell suspension into centrifugal tubes with a pipette under sterile conditions, then the cell suspension was centrifuged for 3 minutes at 1300 rpm. Discarded the supernatant lightly and added fresh culture medium. Mixed the cells by pipetting, then transferred the cells into culture flasks, and put them into the $CO_2$ incubator. Changed the culture medium once after 24 hours.
2) Cell Culture
Human prostate cancer cells (DU145, PC-3) were cultured in a medium containing RPMI1640 basic medium supplemented with 10% heat-inactivated FBS, 100 IU/mL penicillin, 100 µg/mL streptomycin and 1 mmol/L L-glutamine. Human breast carcinoma cells (T47D, MDA-MB231) were cultured in a medium containing RPM11640 basic medium supplemented with 10% heat-inactivated FBS, 5 µg/mL insulin, 100 IU/mL penicillin, 100 µg/mL streptomycin and 1 mmol/L L-glutamine. Human breast carcinoma cells (MCF-7) were cultured in a medium containing DMEM basic medium supplemented with 10% heat-inactivated FBS, 5 µg/mL insulin, 100 IU/mL penicillin, 100 µg/mL streptomycin and 1 mol/L L-glutamine. Murine Lewis lung cancer cells (LL/2), murine melanoma cells (B16FD) and Microvascular Endothelial Cells (MVEC) were cultured in a medium containing DMEM basic medium supplemented with 10% heat-inactivated FBS, 4.5 g/L glucose, 1.5 g/L $NaHCO_3$, 100 IU/mL penicillin, 100 µg/mL streptomycin and 4 mmol/L L-glutamine. All these cell lines were incubated at 37° C. biochemical incubator with 5% $CO_2$ saturated humidity.
3) Cells Passage
After resuscitation, the cells were passed for 2-3 generations till they became stable, then they were used for the experiments. Each passage was based on the standard that all cells were spread over the bottoms of culture flasks.
4) Cells Buried Plate
Cells were digested off from the bottoms of culture flasks with trypsin (0.25%). The cell dissociation buffer was transferred into centrifuge tubes, added medium to stop the digestion, and centrifuged for 3 minutes at 1300 rpm. Discarded the supernatant lightly and added fresh culture medium (5 mL). Mixed the cells by pipetting, then added 10 µL of the cell suspension into the cell counting plate, and adjusted the cell concentration to 2×10⁴ cells/mL. Added 100 μL of the cell suspension to all wells on the 96 well plates, except A1 well as the blank control. Put the plates into the biochemical incubator for 24 hours and to make sure the cells grew along the walls.

5) Adding Drugs to the Cells

The drugs were dissolved in 80 mmol/L DMSO first, and then diluted the drugs with ethanol to 8 mmol/L. The solution was further diluted with the culture medium to different concentrations as 160 μmol/L, 120 μmol/L, 80 μmol/L, 40 μmol/L, 20 μmol/L and 10 μmol/L. Added 100 μL of the drug solution to each well on the 96 well plates. Therefore, the final concentrations of the drugs that were added to the cells were 80 μmol/L, 40 μmol/L, 20 μmol/L, 10 μmol/L and 5 μmol/L, and each concentration were repeated in three parallel wells. Put the culture plates into the biochemical incubator to culture continuously for 4 days.

6) Using the MTT Method to Study the Growth Inhibitory Activity of the Cells

Added 50 μL MTT liquids (2 mg/mL) into each well, put the culture plates into the biochemical incubator for 4 h, discarded MTT liquids (TCC), added 200 μL DMSO, then oscillated for 10 minutes on the magnetic oscillator to make sure that the survived cells and the reaction product of MTT were fully dissolved. Detected and recorded the absorbance (OD) values of each well at the wavelength of 570 nm using the microplate reader. The OD values of cells without tested drugs were used as control. The cell growth inhibition rates under each drug concentration were calculated by the following formula. $IG_{50}$ value is used in herein to demonstrate the inhibitory effect on the growth of cancer cells (the concentration of tested drugs to inhibit growth of cancer cell by 50%).

Inhibition rate of growth(%)=(1−The absorbance(*OD*) of cells with tested drugs/The absorbance(*OD*)of the blank control group)×100%

The absorbance (OD) of cells with tested drugs: OD value is measured with the test drugs.

The absorbance (OD) of the blank control group: OD value is measured without the test drugs.

7) The Growth Inhibition Activity of Compounds on Microvascular Endothelial Cells (MVEC) (Table 1).

TABLE 1 the $IG_{50}$ list of compounds on inhibiting growth of MVEC

| Example number | IG50 (μmol/L) |
|---|---|
| Example 13 | 3.17 |
| Example 15 | 15.50 |
| Example 22 | 17.35 |
| Example 23 | 16.06 |
| Example 25 | 16.8 |
| Example 27 | 9.09 |
| Example 32 | 14.34 |
| Example 33 | 26.54 |
| Example 36 | 23.28 |
| Example 40 | 31.65 |
| Example 47 | 27.93 |
| Example 48 | 16.85 |
| Example 49 | 25.34 |
| Example 53 | 37.98 |
| Example 55 | 14.77 |
| Example 56 | 16.34 |
| Example 63 | 28.84 |
| Example 65 | 11.02 |
| Example 66 | 38.59 |
| Example 67 | 21.38 |
| Example 69 | 24.86 |
| Example 70 | 23.19 |
| Example 72 | 7.98 |
| Example 73 | 15.22 |
| Example 76 | 23.05 |
| Example 77 | 17.08 |
| Example 78 | 10.71 |
| Example 79 | 9.56 |
| Example 80 | 7.93 |
| Example 81 | 10.33 |
| Example 82 | 9.19 |
| Example 83 | 10.50 |
| Example 84 | 5.25 |
| Example 85 | 8.06 |
| Example 86 | 4.28 |
| Example 87 | 11.49 |
| Example 88 | 12.68 |
| Example 89 | 9.85 |
| Example 90 | 10.78 |
| Example 91 | 10.83 |
| Example 92 | 7.24 |
| Example 93 | 11.72 |
| PTK787 | 38.15 |

8) The Growth Inhibition Effect of Compounds on Human Breast Carcinoma Cells (T47D, MDA-MB231, MCF-7), Human Prostate Cancer (DUI45, PC-3), Murine Lewis Lung Cancer Cells (LL/2), Murine Melanoma Cells(B16F0) and Human Umbilical Vein Endothelial Cells (HUVEC) (Table 2).

TABLE 2 the $IG_{50}$ list of compounds on inhibiting growth of B16F0, LL/2, DU145, PC-3, T47D, MCF-7, MDA-MB231

| Example number | IG50 (μmol/L) | | | | | | |
|---|---|---|---|---|---|---|---|
| | B16F0 | HUVEC | LL/2 | DU145 | PC-3 | T47D | MCF-7 | MDA-MB231 |
| Example 27 | 22.15 | 5.06 | 15.70 | 15.10 | 15.76 | 18.44 | 6.17 | 19.64 |
| Example 72 | 5.19 | 3.73 | 3.79 | 4.96 | 6.91 | 5.04 | | |
| Example 84 | 4.28 | 3.02 | 4.79 | 5.90 | 6.90 | 5.87 | 3.95 | 5.10 |
| Example 86 | 4.67 | 2.21 | 4.13 | 4.14 | 5.99 | 6.42 | 4.55 | 4.71 |
| PTK787 | 21.45 | >40 | 34.99 | 41.28 | 63.68 | 36.32 | 12.26 | 24.25 |

9) Acute Toxicity Testing

Animals: healthy mice of Kunming species, female and male each account for 50%, and the weights range from 18 to 22 g. All the mice were obtained from the laboratory animal center of Shenyang Pharmaceutical University. Certificate number: Liao Shi He Zi No. 033

Name of tested medicine: Example 27, Example 84 and Example 86.

Medicine preparation: drugs were added in 0.2% Polysorbate 80 (Tween-80) to make suspension. The dosage of tested compounds was indicated with mg/kg.

Administration routes: peritoneal injection, administration volume was 0.1 mL/10 g, and single administration of multi-doses was used.

Test period and Observed index: observed for one week after the administration. The toxic reaction information of the mice was recorded everyday during the observation period. The death of mice was regarded as the principal index. Half lethal doses ($LD_{50}$, mg/kg) of the compounds one week after the drug administration were calculated according to the method of weighted regression.

10) The Results of Acute Toxicity Testing are Exhibited in Table 3

TABLE 3 value of $LD_{50}$ of tested compounds

| Example number | $LD_{50}$ (mg/kg) | 95% Confidence interval of $LD_{50}$ |
|---|---|---|
| Example 27 | 733.2 | 785.2-677.5 |
| Example 84 | 423.5 | 358.6-487.1 |
| Example 86 | 292.1 | 224.8-358.4 |

Activity test by chick chorioallantoic membrane method

1) Several pieces of fertilized embryos were put in a 38° C. hatch box with a 95% humidity to hatch for 6 days (air chamber-side up and flipped four times a day)
2) Used a pencil to draw the periphery of the air chamber.
3) Wiped the chicken embryos with 75% alcohol and let the embryos stand for 15 minutes.
4) Marked a 2×2 cm window on the top of the air chamber in the embryos, then cut and grinded the window with scissors, blew away all the dust on the shell, and peeled off the shell at the window.
5) Added a few drops of normal saline on the shell membrane. After the shell membrane became wet, tore it open with ophthalmological tweezers so to expose the chorioallantoic membrane.
6) Added 5 uL of selected medicine to a 0.5×0.5 cm cellulose membrane sterilized by high pressure, then set the membrane on the part of the chorioallantoic membrane with fewer vessels
7) Closed the window, and put the embryos back into the hatch box to hatch for 2 days.
8) Opened the transparent tape, and then opened the mixed cellulose membrane lightly with a tweezers. Measured the avascular area and took photographs.

The results of conventional record and evaluation criteria: (−) normal growth of blood vessels at covered zone or the zone without vessels is less than 4 mm; (☆) the avascular zone ranges from 4 to 6 mm; (☆☆) the avascular zone is more than 6 mm.

9) The inhibitory effect of compounds on the growth of chorioallantoic membrane vessels is exhibited in table 4.

TABLE 4

The inhibitory effect of compounds on the growth chorioallantoic membrane vessels

| Number of Examples | The inhibitory effect on the growth of chorioallantoic membrane vessels |
|---|---|
| Example 03 | Significant inhibition in two of three samples, Another one exhibits inconspicuous inhibition. |
| Example 04 | The vascular growth is abundant |
| Example 06 | One of the two samples exhibits significant fracture, The other gets thin but phenomenon is not significant. |
| Example 07 | Two samples exhibit significant inhibition ring |
| Example 15 | Both of the samples exhibit inhibition zone and the zone of one sample is larger. |
| Example 19 | Vessels are broken in one of two samples, the other exhibits significant inhibition ring. |
| Example 20 | One of the two samples exhibits significant inhibition, and the other exhibits no vessels at the exposed sites of chorioallantoic membrane |
| Example 21 | The vessels covered by paper become thinner, and another embryo is dead. |
| Example 22 | The vessels are fractured at the central part that is covered by paper. |
| Example 23 | The vessels covered by paper become thinner and fewer. |
| Example 34 | One of the two samples exhibits significant inhibition zone, and the other exhibits inhibition ring at the central part of the paper |
| Example 36 | One sample exhibits no vascular growth at the zone covered by paper. |
| Example 38 | One embryo is dead. |
| Example 39 | One embryo is dead, and the other exhibits no significant inhibition |
| Example 40 | One of the two samples exhibits inhibition |
| Example 41 | One embryo is dead, and the other exhibits no significant inhibition |
| Example 42 | One of the two samples exhibits inhibition |
| Example 47 | The vessels in the paper covered zone become fewer, and inhibition ring appears. |
| Example 50 | One of the two samples exhibits inhibition ring. |
| Example 51 | The samples exhibit significant inhibition ring. |
| Example 53 | Both of the samples exhibit inhibition ring at the central part of the paper, and one sample exhibits significant inhibition. |

TABLE 4-continued

The inhibitory effect of compounds on the growth chorioallantoic membrane vessels

| Number of Examples | The inhibitory effect on the growth of chorioallantoic membrane vessels |
|---|---|
| Example 59 | The vessels become fewer, but not thinner. The medicine precipitates out. |
| Example 61 | One sample exhibits inhibition ring at the zone covered by paper. |
| Example 62 | The embryo is dead. |
| Example 67 | The embryo is dead. |
| Example 68 | Two samples exhibit inhibition at the zone covered by paper. |
| Example 74 | The vessels become rare and are fractured at the zone covered by paper. |
| Example 75 | Smaller inhibition ring appears at the zone covered by paper. |
| Example 76 | The vessels become rare at the zone covered by paper. |
| Example 90 | One exhibits no inhibition, and embryo of the other sample is dead. |
| Example 91 | The vessels of one sample become thinner and fewer at the zone covered by paper, and the other exhibits no inhibition. |
| Example 92 | One of the two samples exhibits significant vascular inhibition. |
| Example 93 | One of the two samples exhibits death of the embryo, and the other exhibits no significant inhibition. |
| PTK787 | There is no vascular growth. |

VEGFR-2 Inhibition Rate Test

VGFR-2 Kinase Assay Kit, purchased from CST with a serial number of 7788, was used to evaluate the inhibitory effect of the compounds on VEGFR-2. Experiments were carried out according to the Kit instruction as the follows 1) Added 10 μL 10 mM ATP to 1.25 ml 6 μM substrate peptide, and diluted the mixture to 2.5 mL with pure water to prepare the reaction solution of 2×ATP/Substrate (ATP=40 μM, Substrate=3 μm).

2) Quickly moved VGFR-2 Kinase from −80° C. to the ice to be thawed.

3) Centrifuged at 4° C. shortly, then the liquid was centrifuged to the bottoms of the containers and moved back on the ice.

4) Added 10 μL 1.25 mM DTT into 2.5 mL HTScan® Tyrosin Kinase Buffer (240 mM HEPES, pH=7.5, 20 mM MgCl$_2$, 20 mM MnCl$_2$, 12 μM Na$_3$VO$_4$) to prepare DTT/Kinase buffer solution.

5) Added 0.6 mL DTT/Kinase buffer solution to a tube containing the kinase to prepare 4× Reaction solution (Kinase=8 ng/μL).

6) Diluted 12.5 μL of selected compound by the same volume, then mixed with 12.5 μL 4× Reaction solution of Kinase, and incubated for 5 minutes at room temperature.

7) Added 25 μL 2× Reaction solution of ATP/Substrate into the above solution.

8) Incubated for 30 minutes at room temperature.

9) Added 50 μL Stop buffer (50 mM EDTA, pH8.0) to each well to stop the reaction.

10) Added 25 μL reaction solution and 75 μL pure water to Streptavidin coated plates and incubated for 60 minutes at room temperature.

11) Diluted Phospho-Tyrosin mAb with PBS/T containing 1% BSA to one thousandth, and added 100 uL of the diluted Ab to each well.

12) Incubated for 60 minutes at room temperature.

13) Washed the plate three times with 200 μL PBS/T for each well.

Detection of Colorimetric ELISA

14) Secondary antibody was diluted with PBS/T containing 1% BSA marked by HRP (IgG of anti-rat diluted to 1/500, and IgG of anti-rabbit diluted to 1/1000).

15) Added 100 μL diluted secondary antibody to each well.

16) Incubated for 30 minutes at room temperature.

17) Washed the plate five times with 200 μL PBS/T for each well.

18) Added 100 μL TMB substrate to each well.

19) Incubated for 15 minutes at room temperature.

20) Added 100 μL Sulfuric acid solution (2N) to each well to stop the reaction, and mixed evenly.

21) Detected the absorbance at 450 nm with Microplate Reader and calculated enzyme inhibition rate.

The inhibition rates of compounds on VEGFR-2 are exhibited in Table 5

TABLE 5 inhibition rates of compounds on VEGFR-2

| Number of Examples | Kinase inhibition rate |
|---|---|
| Example 01 | 3.47 |
| Example 02 | −22.99 |
| Example 03 | 19.78 |
| Example 04 | 12.83 |
| Example 05 | −5.34 |
| Example 06 | −33.42 |
| Example 07 | −17.64 |
| Example 08 | −6.95 |
| Example 09 | 1.60 |
| Example 10 | −2.67 |
| Example 11 | −4.27 |
| Example 12 | 9.09 |
| Example 13 | −9.89 |
| Example 14 | −0.80 |
| Example 15 | 10.69 |
| Example 16 | −12.03 |
| Example 17 | −5.34 |
| Example 18 | 3.20 |
| Example 19 | −56.68 |
| Example 20 | 10.96 |
| Example 21 | 2.40 |
| Example 22 | 0.80 |
| Example 23 | 12.56 |
| Example 24 | 12.03 |
| Example 25 | 5.61 |
| Example 26 | 9.89 |
| Example 27 | 12.03 |
| Example 28 | 45.98 |
| Example 29 | 35.77 |
| Example 34 | 37.34 |
| Example 35 | 24.66 |
| Example 36 | 49.20 |
| Example 37 | 38.44 |
| Example 38 | 45.50 |
| Example 39 | 46.67 |
| Example 40 | 46.78 |
| Example 41 | 48.87 |
| Example 42 | 44.10 |
| Example 43 | 43.56 |

TABLE 5-continued inhibition rates of compounds on VEGFR-2

| Number of Examples | Kinase inhibition rate |
|---|---|
| Example 44 | −22.45 |
| Example 45 | 19.78 |
| Example 46 | −0.53 |
| Example 47 | 10.69 |
| Example 48 | −21.65 |
| Example 49 | 18.98 |
| Example 50 | −9.35 |
| Example 51 | −18.71 |
| Example 52 | 2.13 |
| Example 53 | 11.22 |
| Example 54 | 3.20 |
| Example 55 | −0.53 |
| Example 56 | −3.74 |
| Example 57 | 10.42 |
| Example 58 | −5.61 |
| Example 59 | 11.49 |
| Example 60 | 7.75 |
| Example 61 | 3.58 |
| Example 66 | −10.15 |
| Example 62 | 18.10 |
| Example 63 | −9.97 |
| Example 64 | 10.73 |
| Example 67 | 0.26 |
| Example 68 | 1.51 |
| Example 69 | −14.75 |
| Example 70 | 16.65 |
| Example 71 | 21.14 |
| Example 72 | −14.70 |
| Example 73 | 2.40 |
| Example 74 | 0.26 |
| Example 75 | 0.80 |
| Example 76 | 9.35 |
| Example 77 | 14.19 |
| Example 83 | 23.56 |
| Example 79 | 29.83 |
| Example 80 | 30.75 |
| Example 81 | −6.44 |
| Example 82 | 30.08 |
| Example 78 | 15.87 |
| Example 84 | 40.0 |
| Example 85 | 17.24 |
| Example 86 | 29.93 |
| Example 87 | 29.67 |
| Example 88 | 2.39 |
| Example 89 | −0.25 |
| Example 90 | 12.08 |
| Example 91 | 31.567 |
| Example 92 | 30.80 |
| Example 93 | 5.27 |

Rat Aortic Ring Assay 1) 6 week old SD mice (Sprague Dawley) were selected for the experiments. Cleaned abdominal skin with 75% ethanol to disinfect, and then anesthetized the mice with ether,
2) Carefully removed the abdominal aortas and transferred the aortas to normal saline. Excessive vascular tissues were carefully removed with scissors.
3) The aortas were rinsed with normal saline until no blood stain remained.
4) Sectioned the aortas into one millimeter depth arterial slices with ophthalmological scissors.
5) Add 50 µL pre-thawed Matrigel to each well of the pre-cooled 96 well cell culture plates, and embedded the ring-shaped mouse aortas in collagen gel.
6) Incubated for 60 minutes at 37° C. to solidificate the gel.
7) Added DMEM culture solution containing 10% FBS, along with different concentrations of the selected compounds into the wells and cultured in the incubator. Every compound was repeated in no less than 3 wells.
8) Replaced with the fresh medium and changed the medicine once on the third day.
9) Took out the pates on the sixth day, and observed the vascular growth with Microscope (OLYMPUS, DP70, Japan) and took photographs(×100). Randomly chose 3 arterial rings to photograph and calculated the area covered by micro-vascular with Image Pro Plus software. The inhibition rate is calculated as:

$$\text{Inhibition rate}(\%) = \frac{area_{controlhole} - area_{injectionhole}}{area_{controlhole}} \times 100\%$$

Evaluation criteria: ☆inhibition rate<30-60%; ☆☆inhibition rate 60-90%; ☆☆☆inhibition rate>90%.

TABLE 6

The activity result of Rat Aortic Ring Assay

| Patent number | Rat Aortic Ring Assay (10 ug/ml) |
|---|---|
| Example 3 | No significant inhibition |
| Example 6 | No significant inhibition |
| Example 7 | No significant inhibition |
| Example 13 | No significant inhibition |
| Example 15 | About 30% inhibition compared with the blank control |
| Example 17 | No significant inhibition compared with the blank control |
| Example 18 | No significant inhibition |
| Example 19 | No significant inhibition compared with the blank control. |
| Example 20 | Cell proliferation and migration were not significantly affected, but endothelial cell morphology changed as the cells were elongated and there were fewer cell tubes formation. |
| Example 21 | No significant inhibition |
| Example 22 | Cell proliferation and migration were affected. Endothelial cell morphology changed as the cells were elongated and there were fewer cell tubes formation. |
| Example 23 | Cell morphology was similar to D10, and cells were linear. |
| Example 28 | Less vessel formation; about 40% inhibition |
| Example 34 | Compared with blank control, vascular growth was rare and inhibition rate was more than 80% |
| Example 35 | Less vessel formation; about 40% inhibition |
| Example 36 | Almost complete inhibition (10 µg/mL) |

TABLE 6-continued

The activity result of Rat Aortic Ring Assay

| Patent number | Rat Aortic Ring Assay (10 ug/ml) |
|---|---|
| Example 37 | Inhibition was strong in the first 3 days, and weak in later 4 days. |
| Example 38 | No significant inhibition |
| Example 39 | No significant inhibition |
| Example 40 | No significant inhibition |
| Example 41 | No significant inhibition |
| Example 42 | Less vessel formation; about 40% inhibition |
| Example 43 | No significant inhibition |
| Example 47 | No significant inhibition |
| Example 50 | No significant inhibition compared with the blank control |
| Example 51 | No significant inhibition |
| Example 53 | No significant inhibition |
| Example 59 | No significant inhibition |
| Example 61 | No significant inhibition |
| Compound 62 | No significant inhibition |
| Example 64 | More than 50% inhibition, affecting cell migration |
| Example 67 | More than 50% inhibition, affecting cell migration |
| Example 68 | Vascular growth is significantly inhibited |
| Example 70 | More than 50% inhibition, affecting cell migration |
| Example 74 | Vessel density was small, cells were elongated and cell proliferation might be affected. |
| Example 75 | No significant inhibition |
| Example 76 | No significant inhibition |
| Example 77 | Micro-vascular growth was significantly inhibited, affecting cell tubes formation and might affect cell proliferation |
| Example 78 | No significant inhibition in the previous 3 days, but vascular ring is dead on the 6th day |
| Example 79 | Almost complete inhibition (10 μg/mL), vascular ring was dead |
| Example 80 | Almost complete inhibition (10 μg/mL), vascular ring was dead. |
| Example 81 | Almost complete inhibition (10 μg/mL), vascular ring was dead. |
| Example 82 | Compared with blank control, vascular growth was rare and inhibition rate was more than 80% |
| Example 83 | No significant inhibition |
| Example 84 | Almost complete inhibition (10 μg/mL), vascular ring was dead |
| Example 85 | No significant inhibition |
| Example 86 | Almost complete inhibition (10 μg/mL), vascular ring was dead |
| Example 87 | Almost complete inhibition (10 μg/mL), vascular ring was dead |
| Example 88 | Almost complete inhibition (10 μg/mL), vascular ring was dead |
| Example 91 | No significant inhibition |
| Example 92 | More than 50% inhibition, affecting cell migration |
| Example 94 | No significant inhibition |
| Example 95 | Vascular growth was significantly inhibited, vascular ring was dead. |
| Example 96 | Vessel formation became less, about 30% inhibition |

The invention claimed is:

1. Compounds of Formula I:

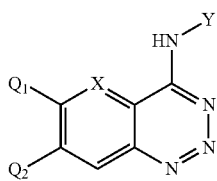

I wherein:

X is CH, $Q_1$ and $Q_2$ are same or different, and independently selected from: $C_{1-5}$ alkoxy optionally substituted with $R_1$, or X is N, $Q_1$ and $Q_2$ are same or different, and independently selected from: H, halogen, or $C_{1-5}$ alkoxy optionally substituted with $R_1$, wherein the $R_1$ is halogen, $C_3$-$C_7$-cycloalkyl, 5-10 numbered heterocycle, or 5-10 numbered heteroaryl, the cycloalkyl optionally has 1-2 carbon-carbon double bonds or triple bonds, and the heterocycle or heteroaryl has 1-4 hetero atoms selected from N, O, or S, Y is phenyl; wherein the phenyl is optionally substituted by one to three same or different $R_2$ independently selected from halogen, $NO_2$, CN, $CF_3$, $-OCF_3$, $C_{1-4}$-alkyl, $C_{1-4}$-alkoxymethyl, N,N-di-$C_{1-4}$-alkylamino or $C_3$-$C_7$-cycloalkyl, and the cycloalkyl optionally has 1-2 carbon-carbon double bonds or triple bonds, and optical isomers, pharmaceutically acceptable salts and hydrates thereof.

2. The compounds of formula I according to claim 1, wherein $Q_1$ is $-OCH_3$, X is CH, Y is phenyl optionally substituted by one to three same or different $R_2$, $Q_2$ is $C_{1-5}$-alkoxy substituted with $R_1$, wherein $R_2$ is halogen, $NO_2$, CN, $CF_3$, $-OCF_3$, $C_{1-4}$-alkyl, $C_{1-4}$-alkoxymethyl, N,N-di-$C_{1-4}$-alkylamino or $C_3$-$C_7$-cycloalkyl, and the cycloalkyl optionally has 1-2 carbon-carbon double bonds or triple bonds, $R_1$ is halogen, $C_3$-$C_7$-cycloalkyl, 5-10 numbered heterocycle, or 5-10 numbered heteroaryl, the cycloalkyl optionally has 1-2 carbon-carbon double bonds or triple bonds, and the heterocycle or heteroaryl has 1-4 hetero atoms selected from N, O, or S.

3. The compounds of formula I according to claim 1, wherein $Q_1$ is Cl, $Q_2$ is H, X is N, Y is phenyl optionally substituted by one to three same or different $R_2$, wherein $R_2$ is halogen, NO₂, CN, CF₃, —OCF₃, $C_{1-4}$-alkyl, $C_{1-4}$-alkoxymethyl, N,N-di-$C_{1-4}$-alkylamino or $C_3$-$C_7$-cycloalkyl, and the cycloalkyl optionally has 1-2 carbon-carbon double bonds or triple bonds, and optical isomers, pharmaceutically acceptable salts and hydrates thereof.

4. The compounds of formula I according to claim 1, which is selected from the group consisting of:

6-methoxy-7-n-butoxy-4-anilino-benzo[d][1,2,3]triazine;
6-methoxy-7-n-butoxy-4-(3-fluoro-4-bromoanilino)-benzo[d][1,2,3]triazine;
6-methoxy-7-n-butoxy-4-(3,5-dichloroanilino)-benzo[d][1,2,3]triazine;
6-methoxy-7-n-butoxy-4-(3,5-difluoroanilino)-benzo[d][1,2,3]triazine;
6-methoxy-7-n-butoxy-4-(3,4-dichloroanilino)-benzo[d][1,2,3]triazine;
6-methoxy-7-n-butoxy-4-(4-chloroanilino)-benzo[d][1,2,3]triazine;
6-methoxy-7-n-butoxy-4-(3-trifluoromethylanilino)-benzo[d][1,2,3]triazine;
6-methoxy-7-n-butoxy-4-(4-trifluoromethylanilino)-benzo[d][1,2,3]triazine;
6-methoxy-7-n-butoxy-4-(3-trifluoromethoxyanilino)-benzo[d][1,2,3]triazine;
6-methoxy-7-n-butoxy-4-(4-trifluoromethoxyanilino)-benzo[d][1,2,3]triazine;
6-methoxy-7-n-butoxy-4-(3-chloroanilino)-benzo[d][1,2,3]triazine;
6-methoxy-7-n-butoxy-4-(3-chloro-4-fluoroanilino)-benzo[d][1,2,3]triazine;
6-methoxy-7-n-butoxy-4-(3-trifluoromethyl-4-fluoroanilino)-benzo[d][1,2,3]triazine;
6-methoxy-7-n-butoxy-4-(2-fluoroanilino)-benzo[d][1,2,3]triazine;
6-methoxy-7-n-butoxy-4-(3-bromoanilino)-benzo[d][1,2,3]triazine;
6-methoxy-7-n-butoxy-4-(4-fluoroanilino)-benzo[d][1,2,3]triazine;
6-methoxy-7-n-butoxy-4-(4-methylanilino)-benzo[d][1,2,3]triazine;
6-methoxy-7-ethoxy-4-anilino-benzo[d][1,2,3]triazine;
6-methoxy-7-ethoxy-4-(3-fluoro-4-bromoanilino)-benzo[d][1,2,3]triazine;
6-methoxy-7-ethoxy-4-(3,5-dichloroanilino)-benzo[d][1,2,3]triazine;
6-methoxy-7-ethoxy-4-(3,5-difluoroanilino)-benzo[d][1,2,3]triazine;
6-methoxy-7-ethoxy-4-(3,4-dichloroanilino)-benzo[d][1,2,3]triazine;
6-methoxy-7-ethoxy-4-(4-chloroanilino)-benzo[d][1,2,3]triazine;
6-methoxy-7-ethoxy-4-(3-trifluoromethylanilino)-benzo[d][1,2,3]triazine;
6-methoxy-7-ethoxy-4-(4-trifluoromethylanilino)-benzo[d][1,2,3]triazine;
6-methoxy-7-ethoxy-4-(3-trifluoromethoxyanilino)-benzo[d][1,2,3]triazine;
6-methoxy-7-ethoxy-4-(4-trifluoromethoxyanilino)-benzo[d][1,2,3]triazine;
6-methoxy-7-ethoxy-4-(3-chloroanilino)-benzo[d][1,2,3]triazine;
6-methoxy-7-ethoxy-4-(3-chloro-4-fluoroanilino)-benzo[d][1,2,3]triazine;
6-methoxy-7-ethoxy-4-(3-trifluoromethyl-4-fluoroanilino)-benzo[d][1,2,3]triazine;
6-methoxy-7-ethoxy-4-(2-fluoroanilino)-benzo[d][1,2,3]triazine;
6-methoxy-7-ethoxy-4-(3-bromoanilino)-benzo[d][1,2,3]triazine;
6-methoxy-7-ethoxy-4-(4-methylanilino)-benzo[d][1,2,3]triazine;
6-methoxy-7-pentyloxy-4-anilino-benzo[d][1,2,3]triazine;
6-methoxy-7-pentyloxy-4-(3-fluoro-4-bromoanilino)-benzo[d][1,2,3]triazine;
6-methoxy-7-pentyloxy-4-(3,5-dichloroanilino)-benzo[d][1,2,3]triazine;
6-methoxy-7-pentyloxy-4-(3,5-difluoroanilino)-benzo[d][1,2,3]triazine;
6-methoxy-7-pentyloxy-4-(3,4-dichloroanilino)-benzo[d][1,2,3]triazine;
6-methoxy-7-pentyloxy-4-(4-chloroanilino)-benzo[d]1,2,3]triazine;
6-methoxy-7-pentyloxy-4-(3-trifluoromethylanilino)-benzo[d][1,2,3]triazine;
6-methoxy-7-pentyloxy-4-(4-trifluoromethylanilino)-benzo[d][1,2,3]triazine;
6-methoxy-7-pentyloxy-4-(3-trifluoromethoxyanilino)-benzo[d][1,2,3]triazine;
6-methoxy-7-pentyloxy-4-(4-trifluoromethoxyanilino)-benzo[d][1,2,3]triazine;
6-methoxy-7-pentyloxy-4-(3-chloroanilino)-benzo[d][1,2,3]triazine;
6-methoxy-7-pentyloxy-4-(3-chloro-4-fluoroanilino)-benzo[d][1,2,3]triazine;
6-methoxy-7-pentyloxy-4-(3-trifluoromethyl-4-fluoroanilino)-benzo[d][1,2,3]triazine;
6-methoxy-7-pentyloxy-4-(2-fluoroanilino)-benzo[d][1,2,3]triazine;
6-methoxy-7-pentyloxy-4-(3-bromoanilino)-benzo[d][1,2,3]triazine;
6-methoxy-7-pentyloxy-4-(4-fluoroanilino)-benzo[d][1,2,3]triazine;
6-methoxy-7-pentyloxy-4-(4-methylanilino)-benzo[d][1,2,3]triazine;
6-methoxy-7-chloropropoxy-4-anilino-benzo[d][1,2,3]triazine;
6-methoxy-7-chloropropoxy-4-(3-fluoro-4-bromoanilino)-benzo[d][1,2,3]triazine;
6-methoxy-7-chloropropoxy-4-(3,5-dichloroanilino)-benzo[d][1,2,3]triazine;
6-methoxy-7-chloropropoxy-4-(3,5-difluoroanilino)-benzo[d][1,2,3]triazine;
6-methoxy-7-chloropropoxy-4-(3,4-dichloroanilino)-benzo[d][1,2,3]triazine;
6-methoxy-7-chloropropoxy-4-(4-chloroanilino)-benzo[d][1,2,3]triazine;
6-methoxy-7-chloropropoxy-4-(3-trifluoromethylanilino)-benzo[d][1,2,3]triazine;
6-methoxy-7-chloropropoxy-4-(4-trifluoromethylanilino)-benzo[d][1,2,3]triazine;
6-methoxy-7-chloropropoxy-4-(3-trifluoromethoxyanilino)-benzo[d][1,2,3]triazine;
6-methoxy-7-chloropropoxy-4-(4-trifluoromethoxyanilino)-benzo[d][1,2,3]triazine;
6-methoxy-7-chloropropoxy-4-(3-chloroanilino)-benzo[d][1,2,3]triazine;
6-methoxy-7-chloropropoxy-4-(3-chloro-4-fluoroanilino)-benzo[d][1,2,3]triazine;
6-methoxy-7-chloropropoxy-4-(3-trifluoromethyl-4-fluoroanilino)-benzo[d][1,2,3]triazine;

6-methoxy-7-chloropropoxy-4-(2-fluoroanilino)-benzo[d][1,2,3]triazine;
6-methoxy-7-chloropropoxy-4-(3-bromoanilino)-benzo[d][1,2,3]triazine;
6-methoxy-7-chloropropoxy-4-(4-fluoroanilino)-benzo[d][1,2,3]triazine;
6-methoxy-7-chloropropoxy-4-(4-methylanilino)-benzo[d][1,2,3]triazine;
6-chloro-4-anilino-pyrido[3,2-d][1,2,3]triazine;
6-chloro-4-(3-fluoro-4-bromo-anilino)-pyrido[3,2-d][1,2,3]triazine;
6-chloro-4-(3,5-dichloroanilino)-pyrido[3,2-d][1,2,3]triazine;
6-chloro-4-(3,5-difluoroanilino)-pyrido[3,2-d][1,2,3]triazine;
6-chloro-4-(3,4-dichloroanilino)-pyrido[3,2-d][1,2,3]triazine;
6-chloro-4-(4-chloroanilino)-pyrido[3,2-d][1,2,3]triazine;
6-chloro-4-(3-trifluoromethylanilino)-pyrido[3,2-d][1,2,3]triazine;
6-chloro-4-(4-trifluoromethylanilino)-pyrido[3,2-d][1,2,3]triazine;
6-chloro-4-(3-trifluoromethoxyanilino)-pyrido[3,2-d][1,2,3]triazine;
6-chloro-4-(4-trifluoromethoxyanilino)-pyrido[3,2-d][1,2,3]triazine;
6-chloro-4-(3-chloroanilino)-pyrido[3,2-d][1,2,3]triazine;
6-chloro-4-(3-chloro-4-fluoroanilino)-pyrido[3,2-d][1,2,3]triazine;
6-chloro-4-(3-trifluoromethyl-4-fluoro-anilino)-pyrido[3,2-d][1,2,3]-triazine;
6-chloro-4-(2-fluoroanilino)pyrido[3,2-d][1,2,3]triazine;
6-chloro-4-(3-bromoanilino)pyrido[3,2-d][1,2,3]triazine;
6-chloro-4-(4-fluoroanilino)pyrido[3,2-d][1,2,3]triazine;
6-methoxy-7-(3-morpholinopropoxy)-4-(3-chloro-4-fluoroanilino)-benzo[d][1,2,3]triazine;
6-methoxy-7-(3-(piperidin-1-yl)propoxy)-4-(3-chloro-4-fluoroanilino)-benzo[d][1,2,3]triazine hydrochloride;
6-methoxy-7-(3-(4-methylpiperazin-1-yl)propoxy)-4-(3-chloro-4-fluoroanilino)-benzo[d][1,2,3]triazine hydrochloride;
6-methoxy-7-(3-(1H-imidazol-1-yl)propoxy)-4-(3-chloro-4-fluoroanilino)-benzo[d][1,2,3]triazine hydrochloride;
6-methoxy-7-(3-morpholinopropoxy)-4-(3-trifluoromethylanilino)-benzo[d][1,2,3]triazine hydrochloride;
6-methoxy-7-(3-morpholinopropoxy)-4-(4-trifluoromethylanilino)-benzo[d][1,2,3]triazine hydrochloride;
6-methoxy-7-(3-morpholinopropoxy)-4-(3-fluoro-4-bromoanilino)-benzo[d][1,2,3]triazine hydrochloride;
6-methoxy-7-(3-morpholinopropoxy)-4-(3,5-difluoroanilino)-benzo[d][1,2,3]triazine hydrochloride;
6-methoxy-7-(3-morpholinopropoxy)-4-(3-trifluoromethyl-4-fluoroanilino)-benzo[d][1,2,3]triazine hydrochloride;
6-methoxy-7-(3-morpholinopropoxy)-4-(3-trifluoromethoxyanilino)-benzo[d][1,2,3]triazine hydrochloride;
6-methoxy-7-(3-morpholinopropoxy)-4-(4-trifluoromethoxyanilino)-benzo[d][1,2,3]triazine hydrochloride;
6-methoxy-7-(3-(piperidin-1-yl)propoxy)-4-(3-trifluoromethylanilino)-benzo[d][1,2,3]triazine hydrochloride;
6-methoxy-7-(3-(piperidin-1-yl)propoxy)-4-(4-trifluoromethylanilino)-benzo[d][1,2,3]triazine hydrochloride;
6-methoxy-7-(3-(piperidin-1-yl)propoxy)-4-(3-fluoro-4-bromoanilino)-benzo[d][1,2,3]triazine hydrochloride;
6-methoxy-7-(3-(piperidin-1-yl)propoxy)-4-(3,5-difluoroanilino)-benzo[d][1,2,3]triazine hydrochloride;
6-methoxy-7-(3-(piperidin-1-yl)propoxy)-4-(3-trifluoromethyl-4-fluoroanilino)-benzo[d][1,2,3]triazine hydrochloride;
6-methoxy-7-(3-(piperidin-1-yl)propoxy)-4-(3-trifluoromethoxyanilino)-benzo[d][1,2,3]triazine hydrochloride; and
6-methoxy-7-(3-(piperidin-1-yl)propoxy)-4-(4-trifluoromethoxyanilino)-benzo[d][1,2,3]triazine hydrochloride.

5. A pharmaceutical composition comprising the compounds according to any one of claims 1 and 2-4 and a pharmaceutically acceptable carrier and/or adjuvant.

6. The pharmaceutical composition according to claim 5 for treatment of a cancer selected from the group consisting of breast cancer, prostate cancer, lung cancer, and melanoma.

7. A method for treating cancer, comprising administering to a subject in need thereof a therapeutically effective amount of a compound according to any one of claims 1 and 2-4, wherein a method for treating cancer in the subject is provided, and wherein the cancer is selected from the group consisting of breast cancer, prostate cancer, lung cancer, and melanoma.

* * * * *